US011998367B2

(12) United States Patent
Brasch et al.

(10) Patent No.: US 11,998,367 B2
(45) Date of Patent: *Jun. 4, 2024

(54) ASSISTIVE TECHNOLOGY FOR OPERATING NURSING HOMES AND OTHER HEALTH CARE FACILITIES

(71) Applicant: J. BRASCH CO., LLC, Lincoln, NE (US)

(72) Inventors: John Brasch, Lincoln, NE (US); Gordon Smith, Lincoln, NE (US)

(73) Assignee: J. BRASCH CO., LLC, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/364,192

(22) Filed: Jun. 30, 2021

(65) Prior Publication Data

US 2021/0321959 A1    Oct. 21, 2021

Related U.S. Application Data

(63) Continuation of application No. 16/159,412, filed on Oct. 12, 2018, now Pat. No. 11,083,419.
(Continued)

(51) Int. Cl.
*A61B 5/00* (2006.01)
*A61B 5/11* (2006.01)
(Continued)

(52) U.S. Cl.
CPC .............. *A61B 5/746* (2013.01); *A61B 5/002* (2013.01); *A61B 5/0077* (2013.01);
(Continued)

(58) Field of Classification Search
CPC ... A61B 5/1115; A61B 5/0002; A61B 5/1113; A61B 5/1117; G08B 21/02;
(Continued)

(56) References Cited

U.S. PATENT DOCUMENTS 6,028,514 A    2/2000  Lemelson et al.
6,509,830 B1   1/2003  Elliot
(Continued)

FOREIGN PATENT DOCUMENTS

CN    106920372 A    7/2017
EP      0860803 A2   8/1998
(Continued)

OTHER PUBLICATIONS

International Preliminary Report on Patentability, dated Apr. 14, 2020, for International Application No. PCT/US2018/055685, (19 pages).
(Continued)

*Primary Examiner* — Mirza F Alam
(74) *Attorney, Agent, or Firm* — Seed IP Law Group LLP

(57) ABSTRACT

A facility for coordinating the safety care of a person is described. The facility receives sensor output indicating that the person has departed a place of repose. In response to this receiving, the facility establishes an alarm identifying the person, accesses a set of on-duty caregivers, and applies one or more precedence rules to establish a precedence among at least a portion of the set of on-duty caregivers. Until a caregiver has accepted the alarm, for each caregiver in the established precedence, the facility: causes a mobile device carried by the caregiver to render a message notifying the caregiver of the alarm and soliciting the caregiver's acceptance of the alarm; and allows the caregiver an interval of time of a first predetermined length in which to accept the alarm before proceeding to the next caregiver in the established precedence.

14 Claims, 22 Drawing Sheets

Related U.S. Application Data

(60) Provisional application No. 62/691,960, filed on Jun. 29, 2018, provisional application No. 62/643,695, filed on Mar. 15, 2018, provisional application No. 62/580,928, filed on Nov. 2, 2017, provisional application No. 62/572,379, filed on Oct. 13, 2017, provisional application No. 62/572,373, filed on Oct. 13, 2017.

(51) Int. Cl.
*G16H 40/20* (2018.01)
*G16H 50/20* (2018.01)

(52) U.S. Cl.
CPC ........... *A61B 5/1115* (2013.01); *A61B 5/1117* (2013.01); *A61B 5/6891* (2013.01); *G16H 40/20* (2018.01); *G16H 50/20* (2018.01); *A61B 5/0022* (2013.01); *A61B 5/1118* (2013.01); *A61B 5/1126* (2013.01); *A61B 5/6889* (2013.01); *A61B 5/6894* (2013.01); *A61B 5/7267* (2013.01); *A61B 2503/08* (2013.01); *A61B 2505/07* (2013.01); *A61B 2562/0219* (2013.01); *A61B 2562/0247* (2013.01); *A61B 2562/0257* (2013.01)

(58) Field of Classification Search
CPC .. G08B 21/0423; G08B 21/22; G08B 21/043; G08B 21/0446; A61G 2203/34
See application file for complete search history.

(56) References Cited

U.S. PATENT DOCUMENTS

| | | | |
|---|---|---|---|
| 6,512,478 B1 | 1/2003 | Chien | |
| 6,544,200 B1 | 4/2003 | Smith et al. | |
| 6,958,677 B1 | 10/2005 | Carter | |
| 7,242,306 B2 | 7/2007 | Wildman et al. | |
| 7,671,733 B2 | 3/2010 | McNeal et al. | |
| 8,266,742 B2 | 9/2012 | Andrienko | |
| 10,121,346 B2 | 11/2018 | Herbst et al. | |
| 10,567,905 B2 | 2/2020 | Edge et al. | |
| 2001/0022558 A1 | 9/2001 | Karr, Jr. et al. | |
| 2002/0014951 A1 | 2/2002 | Kramer et al. | |
| 2003/0139188 A1 | 7/2003 | Chen et al. | |
| 2004/0020314 A1* | 2/2004 | Tsuchihashi | A61B 5/0507 340/459 |
| 2004/0046668 A1 | 3/2004 | Smith et al. | |
| 2004/0248589 A1* | 12/2004 | Gwon | G01S 5/0252 455/456.4 |
| 2005/0197139 A1 | 9/2005 | Misikangas et al. | |
| 2005/0242928 A1 | 11/2005 | Kirkeby | |
| 2005/0242946 A1 | 11/2005 | Hubbard et al. | |
| 2005/0253704 A1 | 11/2005 | Neuwirth | |
| 2005/0264416 A1 | 12/2005 | Maurer | |
| 2006/0028350 A1* | 2/2006 | Bhai | A61B 5/1115 177/144 |
| 2006/0049936 A1 | 3/2006 | Collins, Jr. et al. | |
| 2006/0158329 A1 | 7/2006 | Burkley et al. | |
| 2007/0005292 A1 | 1/2007 | Jin | |
| 2007/0156031 A1* | 7/2007 | Sullivan | A61B 5/002 600/300 |
| 2007/0229249 A1 | 10/2007 | McNeal et al. | |
| 2007/0247358 A1 | 10/2007 | Alanen et al. | |
| 2007/0288263 A1* | 12/2007 | Rodgers | G08B 21/22 705/2 |
| 2008/0001735 A1 | 1/2008 | Tran | |
| 2008/0033752 A1 | 2/2008 | Rodgers | |
| 2008/0169931 A1 | 7/2008 | Gentry et al. | |
| 2008/0272918 A1* | 11/2008 | Ingersoll | A61B 5/0002 600/595 |
| 2009/0184823 A1 | 7/2009 | Tessier | |
| 2011/0045840 A1 | 2/2011 | Alizadeh-Shabdiz et al. | |
| 2012/0245464 A1 | 9/2012 | Tran | |
| 2012/0245948 A1 | 9/2012 | Nolte et al. | |
| 2013/0053056 A1 | 2/2013 | Aggarwal et al. | |
| 2013/0085771 A1 | 4/2013 | Ghanbari et al. | |
| 2013/0090133 A1 | 4/2013 | D'Jesus Bencci et al. | |
| 2013/0127620 A1 | 5/2013 | Siebers et al. | |
| 2013/0267251 A1 | 10/2013 | Khorashadi et al. | |
| 2013/0283529 A1 | 10/2013 | Hayes et al. | |
| 2013/0321145 A1 | 12/2013 | Ranieri et al. | |
| 2014/0184408 A1 | 7/2014 | Herbst et al. | |
| 2014/0249850 A1 | 9/2014 | Woodson et al. | |
| 2014/0368335 A1 | 12/2014 | Jordan et al. | |
| 2015/0095054 A1 | 4/2015 | Kaigler et al. | |
| 2015/0123786 A1 | 5/2015 | Hasan et al. | |
| 2015/0247913 A1 | 9/2015 | Messier et al. | |
| 2015/0254956 A1 | 9/2015 | Shen et al. | |
| 2015/0269825 A1 | 9/2015 | Tran | |
| 2015/0324539 A1 | 11/2015 | Chiu et al. | |
| 2016/0029160 A1 | 1/2016 | Theurer et al. | |
| 2016/0035196 A1 | 2/2016 | Chan | |
| 2016/0078750 A1 | 3/2016 | King et al. | |
| 2016/0260059 A1 | 9/2016 | Benjamin et al. | |
| 2016/0307429 A1* | 10/2016 | Hood | A61B 5/1115 |
| 2016/0367170 A1 | 12/2016 | Larson et al. | |
| 2016/0371449 A1 | 12/2016 | Brouse | |
| 2017/0004261 A1 | 1/2017 | Abou-Hawil et al. | |
| 2017/0109989 A1 | 4/2017 | Herbst et al. | |
| 2017/0156020 A1 | 6/2017 | Lee et al. | |
| 2017/0195852 A1 | 7/2017 | Theurer et al. | |
| 2017/0258401 A1 | 9/2017 | Volpe | |
| 2017/0325683 A1* | 11/2017 | Larson | A61B 5/002 |
| 2017/0345275 A1* | 11/2017 | Ribble | A61G 7/012 |
| 2018/0004261 A1 | 1/2018 | Ahrens et al. | |
| 2018/0082573 A1 | 3/2018 | Zuckerman et al. | |
| 2018/0144598 A1 | 5/2018 | Herbst et al. | |
| 2018/0333052 A1* | 11/2018 | Chamberlain | G16H 40/67 |
| 2019/0110763 A1 | 4/2019 | Brasch et al. | |
| 2019/0110764 A1 | 4/2019 | Murai et al. | |
| 2019/0110773 A1 | 4/2019 | Brasch et al. | |
| 2019/0166453 A1 | 5/2019 | Edge et al. | |
| 2019/0326015 A1 | 10/2019 | Cannell et al. | |

FOREIGN PATENT DOCUMENTS

| | | |
|---|---|---|
| EP | 2811465 B1 | 5/2016 |
| JP | 2010162151 A | 7/2010 |
| JP | 2017018379 A | 1/2017 |
| MX | 2014006806 A | 12/2014 |
| WO | 2010/111138 A1 | 9/2010 |
| WO | WO 2011113070 A1 | 9/2011 |
| WO | WO 2015117566 A1 | 8/2015 |

OTHER PUBLICATIONS

European Search Report, dated Jun. 18, 2021, for International Patent Application No. PCT/US2018/055685. (10 pages).
European Search Report, dated Jul. 25, 2022, for International Patent Application No. PCT/US2018/055685. (17 pages).
Japanese Office Action, dated Nov. 25, 2022, for Japanese Patent Application No. 2020-520656.(9 pages) (with English Translation).
Office Action, dated May 22, 2023, for Chinese Patent Application No. 201880074945.4. (8 pages).
Office Action, dated Dec. 27, 2023, for Chinese Patent Application No. 201880074945.4. (8 pages).

\* cited by examiner

╭─ 300
┌─────────────────────────────────────────────────────────────────┐
│                                                                 │
│              Resident: Helen T. Smith  ⎫                        │
│              Location: 262a            ⎬ 310                    │
│                                        ⎭                        │
│                                              ╱ 320              │
│   Specify Alarm and Warning Condition for this Resident: ↓      │
│                                                                 │
│                                          ╱─ 321  ╱─ 322 ╱─ 323  │
│   event                                          warning alarm  │
│                                                            ☒╱ 331 │
│   explicit activation                                      □╱ 332 │
│   bed:   weight shift                              ☑       □╱ 333 │
│          partial departure                         ☑       □╱ 334 │
│          full departure                            □       ☑╱ 335 │
│   chair: weight shift                              ☑       □╱ 336 │
│          partial departure                         ☑       □╱ 337 │
│          full departure      ╱─ 341                □       ☑╱ 338 │
│   toilet: no departure for _15_ minutes            ☑       □╱ 339 │
│   room:  departure                                 □       ☑      │
│                                                                 │
│                    •                                            │
│                    •                                            │
│                    •                                   ╱─ 390   │
│                                                  ┌─────────┐    │
│                                                  │ submit  │    │
│                                                  └─────────┘    │
└─────────────────────────────────────────────────────────────────┘

*FIG. 3*

Specify Alarm/Warning Prompting Hierarchy Among Staff:

- [2] Nearest Nursing Assistant — 811
- [3] Nearby Nursing Assistants — 812
- [1] Assigned Nursing Assistant — 813
- [5] Nearest Staff Member — 814
- [6] Nearby Staff Members — 815
- [4] Assigned Staff Members — 816
- [8] Nearest Supervisor — 817
- [8] Assigned Supervisor — 818
- [9] All Hands — 819 submit — 890

ALARM — 900, 910

Resident: Helen T. Smith
Location: 262a  } 920

Type: bed departure — 931

Time: 09:16:30 — 932 accept — 941    decline — 942

Event on Room 108 (a few seconds ago)

Why did they get out of bed/chair?

| | |
|---|---|
| water | ⟋−1011 |
| bathroom | ⟋−1012 |
| food | ⟋−1013 |
| flight | ⟋−1014 |
| family visit | ⟋−1015 |
| other | ⟋−1016 |

Event on Room 108 (a few seconds ago)

⊕ Did a fall occur?

| | |
|---|---|
| yes | ⟋−1021 |
| no | ⟋−1022 |

Event on Room 108 (a few seconds ago)

⊕ Why was there a fall?

| Muscle weakness | /—1031 |
| Difficulty walking | /—1032 |
| Confusion | /—1033 |
| Postural hypotention | /—1034 |
| Painful feet | /—1035 |
| Not seeing well | /—1036 |
| | /—1037 |
| Send | /—1038 |

Event on Room 108 (a seconds ago)

⊕ Was there an injury?

| Injury | /—1041 |
| Non-injury | /—1042 |

*FIG. 10D*

Event on Room 108 (a few seconds ago)

1052 — ⊕ Fall Survey

Why did they get out of bed/chair?
- bathroom

Did a fall occur?
- yes

Why was there a fall?
- Postural hypotention

Was there an injury?
- Injury 1051
submit

ASSISTIVE TECHNOLOGY FOR OPERATING NURSING HOMES AND OTHER HEALTH CARE FACILITIES

CROSS REFERENCE TO RELATED APPLICATIONS

This Application is a Continuation of application Ser. No. 16/159,412, filed on Oct. 12, 2018, which application is related to the following applications, each of which is hereby incorporated by reference in its entirety: U.S. Provisional Patent Application No. 62/572,373, filed on Oct. 13, 2017; U.S. Provisional Patent Application No. 62/572,379, filed on Oct. 13, 2017; U.S. Provisional Patent Application No. 62/580,928, filed on Nov. 2, 2017; U.S. Provisional Patent Application No. 62/643,695, filed on Mar. 15, 2018; and U.S. Provisional Patent Application No. 62/691,960, filed on Jun. 29, 2018. In cases where the present patent application conflicts with an application incorporated here by reference, the present application controls.

BACKGROUND

Nursing homes (sometimes known by other names, such as "care facilities" and "care homes") are residential facilities that provide around-the-clock nursing care for elderly people ("residents," or "patients"). Most residents have health issues that require regular attention. Many residents have limited mobility, and are prone to falls. Some residents suffer from communication deficits or dementia.

In a care facility, residents can be attended by nurses, nursing assistants, other caregivers, supervisors, and a variety of other staff. Such staff can be assigned based on the particular health needs of individual residents; a physical area of the facility in which each resident primarily resides; or on a variety of other bases.

Conventionally, some residents are monitored to determine when they leave their beds, such as residents who are prone to falls. When such a resident's weight leaves the mattress on their bed, an analog pressure switch opens, causing an attached monitor device to emit a loud alarm in the resident's room intended to alert a staff member that the resident has left their bed, and may be at risk of a fall. The alarm may continue until a staff member arrives to check on the resident and cancels the alarm.

BRIEF DESCRIPTION OF THE DRAWINGS

FIG. 3 is a user interface diagram showing a sample user interface presented by the facility in some embodiments to configure for a particular user the conditions that will trigger an alarm or warning.

FIG. 8 is a user interface diagram showing a sample user interface presented by the facility in some embodiments to allow a staff member user to specify a hierarchy among the staff for prompting staff members to respond to resident alarms and warnings.

FIG. 9 is a user interface diagram showing a sample user interface presented by the facility in some embodiments to prompt a staff member to respond to an alarm.

FIGS. 10A-10E are user interface diagrams showing a sample user interface presented by the facility in some embodiments to collect information about a resident alarm or warning and its resolution from the staff member who responded to the alarm or warning.

FIG. 13 is a user interface diagram showing a second sample user interface provided by the facility in some embodiments to show the timing of alarms, warnings, and special or other types of events that occur in a particular care facility or area of a care facility.

DETAILED DESCRIPTION

Overview

Figure 1:
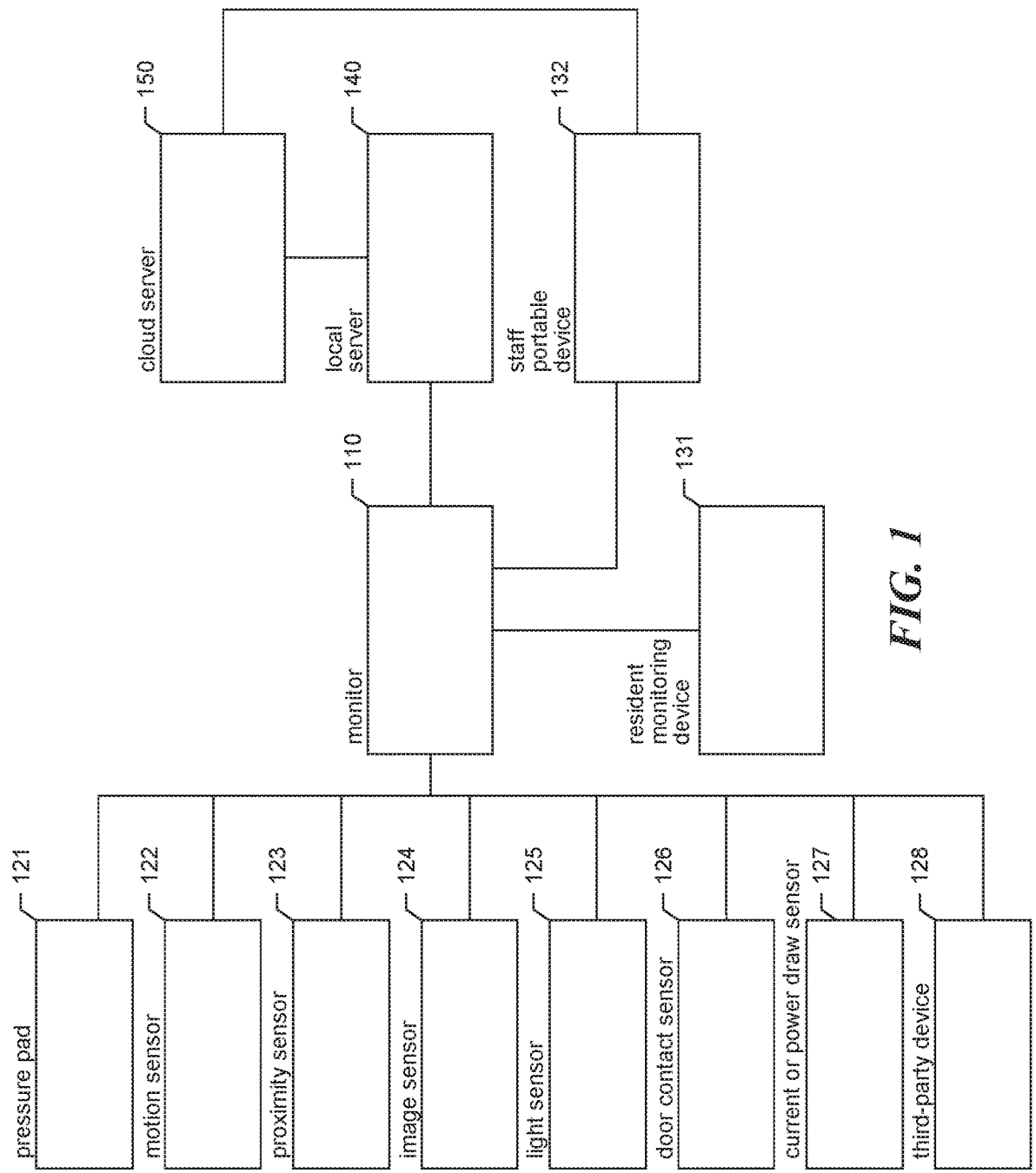
FIG. 1 is a network diagram showing a variety of components that communicate as part of the operation of the facility.

The inventors have recognized that nursing homes and health care facilities of other types would benefit from additional technological assistance. Accordingly, they have conceived and reduced to practice a software and/or hardware facility to assist in the operation of one or more health care facilities ("the facility"). In various embodiments, the facility provides information that enables more thorough, effective, and/or efficient operation of the health care facilities with respect to which it is operated, facilitating data-driven decision making.

In some embodiments, the facility includes one or more high-performance mattress sensor pads that reports a pressure level—in some cases at each of multiple points or regions on the pad. In cases where this multi-point pressure information can be obtained from the pad, the facility uses it to detect restlessness, the probability of future fall from bed; discern nature of bed departure; duration and time in place; sleep stage; and assess repositioning.

In some such embodiments, a circuit included in the pad enables the pad to simulate the "open or closed" behavior of a more basic pad that simply closes a circuit between two conductors if a threshold weight level is exceeded. In particular, this circuit has much lower power requirements than the electrical relay that might otherwise be used.

In some embodiments, the facility uses a variety of other sensor types to monitor the patient's location, position, and safety, such as worn resident tracking device; and/or a fixed motion sensor, proximity sensor, image sensor, and/or light sensor.

In some embodiments, the facility provides a mechanism that allows staff members to configure for each resident the conditions that trigger an alarm. Examples of such conditions include entire resident weight departing bed and/or chair; partial resident weight departing bed and/or chair; explicit alarm activation by resident; failure to depart from bed, chair, and/or toilet for more than a threshold length of time; departure from bed/chair/toilet not followed by arrival at bed/chair/toilet within a threshold length of time; departure from room or portion of room; departure from bed/chair/toilet without returning to a monitored surface for more than a threshold amount of time; etc.

In some embodiments, the facility automatically infers alarm states from data received about the resident from sensors of a variety of types. In some embodiments, the facility uses machine learning techniques to associate sensor outputs proximate in time to explicit alarms with inferred alarm states.

In some embodiments, the facility automatically infers warning states reflecting probable imminent resident needs from data received about the resident from sensors of a variety of types.

In some embodiments, the facility responds to an alarm or warning condition, such as a departure from bed, in a way that summons a staff member without creating a sensory disturbance for that resident, or for other people nearby, such as by selectively prompting staff members using portable devices carried by them. In some embodiments, the facility uses rules and associated information to choose the staff member initially summoned, and to summon additional staff members until a staff member accepts the alarm. In some embodiments, the facility provides a mechanism that allows staff members to configure for each resident which staff members are summoned for alarms raised for the resident, in some cases differently based on the type of the alarm.

In some embodiments, after a staff member accepts the alarm, the facility conducts a survey with the staff member to collect information about the alarm and its resolution. In some embodiments, the facility stores the collected information for further analysis, such as to assess response time and other staff performance metrics; infer information about the resident such as bathroom frequency/schedule; referral suggestions in light of observed resident information; etc.

In some embodiments, the facility provides a mechanism that allows staff members to configure alarm attributes for each resident. Examples of such attributes are silent/audible; visible/non-visible; volume level; duration; sound type; speech/non-speech; etc.

In some embodiments, the facility provides a visual user interface that shows the alarms (or warnings, or alarms and warnings) that have occurred over time relative to a timeline. In various embodiments, these are for a single, selected resident; a group of residents, such as those who reside in a particular area of the health care facility, or are in a particular category of residents based on, for example, their care needs; or all of the residents in the health care facility.

In some embodiments, the facility provides a mechanism that allows staff members to configure voice behavior cues for each resident to suggest actions to him or her, such as "wait by the bed" or "use your walker."

In some embodiments, the facility tracks the physical location of some or more residents, and uses this information to assess whether any resident has left or is in the process of leaving an area in which they should stay. In cases where a resident is, the facility automatically generates an alarm or warning to cause the intervention of a staff member. In some embodiments, the facility tracks the physical location of staff members in the same or similar ways, such as to monitor their performance of rounds, alarm and warning responses, and other responsibilities that involve movement through the health care facility.

By performing in some or all of these ways, the facility assist the operator of a health care facility to provide more consistent, personalized, and valuable care to its residents.

Also, in various embodiments, the facility provides important benefits, as follows:

The SURE® Monitors Patient Risks, Aids a Nurse's Response, and Provides Reports and Documentation.

The SUREnursing™ advisor monitors bed, chair, wheelchair, toilet presence and unexpected movement to rise: It notifies a nurse when a timely response is needed.

The SUREnursing informatics are relevant to understanding, anticipating and responding to patient needs. And reporting outcomes.

More, SUREnursing reports gives supervisors and managers at all levels valuable information they have never seen before about performance.

8 Ways the SUREnursing™ Advisor can Make a Difference

Enhanced Patient Care; Better Informed Individual Care; More Proactive Nursing Management; Better Nursing Collaboration; Better Records, Validation and Reporting; Better General Management; Reduction in Wasted Cost; and Expected Economic Impact.

Enhanced Patient Care

Quiet Notifications: Won't startle the resident, the roommate or the family members. Notifications are received on responder's handheld device, desktop, or laptop.

Facilitates Uninterrupted sleep.

Dignity: Located under the mattress or chair pad, it less likely to attract awareness or unneeded comment.

Comfort: Under mattress/chair pad location moves vinyl sensor away from the skin.

Validates each nurses response to a notification.

Better Informed Staff for Individual Care

Shift change dashboard reviews residents past 24-hour activity pattern. In case of incident, immediate documentation supports details of event.

Notifies designated unit nurses of risk events quietly on their digital device.

Records nursing response to resident risk notification while documenting related nursing presence with the resident.

Escalates notifications to a second responder when the lead responder is busy.

Lets each team member know who is responding.

Helps supervisors with patient care nursing time management by showing periods of higher and lower nursing response activity.

In case of a fall, a questionnaire for the responder provides near time event information supporting further documentation and team collaboration on remedial actions needed.

Helps professional staff to assess dementia resident needs: toileting, hydration, pain, possible UTI, etc.

More Proactive Nursing Management

It starts shift with a computer screen dashboard for a unit or a facility of the last 24 hours of resident bed, chair or wheelchair risk activity with an ability to drill down to specific time and resident.

Provides informatics for real time team collaboration and timely care plan adjustments.

Provides a view of nurses signed in to the SURE® system, and alerts to a supervisor if no one is signed in or confirms an intended notification response in a timely manner.

Provides a desk top overview of SURE system units, availability, location, and functionality, i.e., plugged in, battery status, etc.

Notifies supervisors to residents past due for reposition.

Helps guide direct staff to better self manage time and work flow.

More efficient new-resident care due to immediate baseline data.

More comprehensive information to share with physicians and families.

Better Nursing Collaboration

Individualized data coupled with the professional intuitive skills of those closest to the resident or patient facilitates optimal decision making on a real time basis.

Finding residents in wheel chairs in designated areas.

Facilitates the assignment of individual responsibility and accountability.

Can help evaluations with individual performance information.

Better Records, Validation and Reporting

It starts the day with a computer screen dashboard showing of the last 24 hours of resident risk activity and nursing response.

Helps guide nurse assignments and scheduling by nurse supervisors. Can facilitate custom nursing assignments by specialty, patient need and preference.

Validates daily charting for Medicare and Medicaid documentation.

Supports the screening results and confirms MDS coding.

More efficient new-resident care due to immediate baseline data.

More comprehensive information to share with physicians and families.

Better General Management

It starts the day with a computer dashboard of a facility, or group of facilities summarizing data by faculty and units with the user defined ability to drill down to individual patients and moments in time. Shows fall sand number of notifications to reposition. Probable earlier awareness and better documentation for remedial action.

Validates daily charting for Medicare and Medicaid documentation.

Supports the screening results and confirms MDS coding.

More timely new-resident care planning due to immediate baseline data.

Better data for care plans and survey preparation.

Ever present ready information to share with physicians and families.

Better goal setting and QAPIs related to skin, falls and risk management.

Supports the budget process.

Reduces Wasted Cost

Helps supervisors and DON's with nursing time management by showing periods of higher and lower resident response activity, and relative location.

Provides a focused notification to allow one person to respond to an alert, and escalation if the designated lead responder reports as busy.

With placement of an intelligent sensor pad under a mattress or chair pad time is saved: repositioning the pad; and cleaning the pad when it has not been soiled.

Economic Impact

Creates awareness and documents unnoticed increases in care levels—increased reimbursement.

Better records and validation>faster preparation of MDS—higher star ratings>greater reimbursement>more admissions.

Better reputation in the healthcare network>more admissions>greater revenue.

Improve nursing efficiencies. Less wasted effort.

Improved patient outcomes can lead to more private pay referrals.

Better nursing management can lead to higher nurse retention.

Facility Components

FIG. 1 is a network diagram showing a variety of components that communicate as part of the operation of the facility. While connections between these components are shown by unbroken lines, those skilled in the art will appreciate that components may be connected by wired connections, wireless radio connections, optical connections, etc., or multiple of these.

In some embodiments, the facility includes one or more pressure sensor pads 121, placed on or in or incorporated into a bed, a chair, a couch, a daybed, a wheelchair, a toilet seat, a toilet base, etc. In some embodiments, the pressure sensor pad incorporates a padding element above the pressure sensors, below the pressure sensors, or both.

In some embodiments, the pressure sensor pad has a calibration unit that is permanently or semi-permanently integrated into the pad. In some embodiments, the calibration unit is detachable from the pad, such that the same calibration unit can be used with multiple pads, including multiple pads that are simultaneously deployed in multiple locations within the health care facility, or a series of pads that are deployed in the same health care facility location over time.

In some embodiments, the facility automatically resupplies pressure sensor pads to a health care facility based upon their predicted or sensed end of life. In some embodiments, the resupplied pressure sensing pads are labeled with the particular location in the health care facility of the pad they are to replace, such as a particular room or bed number. In some embodiments, the resupplied pads are mailed in individual packages that are designed to be reused to return the used pad that has been replaced for refurbishing or disposal. In some embodiments, the operator of the facility charges the health care facility a fixed periodic fee for each pad irrespective of when or how frequently they are replaced.

These pressure pads communicate with a monitor device 110, which are in some embodiments provisioned at the level of one for each resident, one for each pair of residents, one for each room, etc. The monitor device communicates information from the pressure pad to a local server 140, where the facility analyzes and processes this information. For example, the local server may recognize in the communicated information an alarm condition or a warning condition, which it uses to notify one or more staff portable devices 132 of an alarm that requires response, in some cases via a cloud server 150. The staff portable devices can be, for example, smart phones, tablets, smart badges or watches, etc. In some embodiments, the local server also communicates with the cloud server 150 to notify staff members or for additional purposes, such as to log information for backup purposes; aggregate and analyze data collected by multiple local servers at different locations; etc. In some embodiments, processing burdens are distributed between the local server and the cloud server on the basis of needed response time, such that tasks that are needed to be performed with a small response time are performed on the local server, while tasks that can tolerate longer response times are performed on the cloud server.

In some embodiments, the monitor device also communicates with additional nearby sensors, such as sensors in the same room: one or more motion sensors 122; one or more proximity sensors 123; one or more image sensors 124; one or more light sensors 125; one or more door contact sensors 126; one or more current or power draw sensors 127 for sensing the level of current or power being drawn by an electrical device plugged into a particular outlet; and one or more third-party devices 128 designed to report information to and/or through the facility and its network. Output from the sensors, too, is conveyed to the local server, and the cloud server, and is there stored and analyzed to identify alarm or warning conditions.

In some embodiments, the monitor device also interacts with the staff portable devices and/or resident tracking devices (such as a pendant or watch worn by a resident) in order to track the location of staff members and residents, respectively.

In some embodiments, some or all of the pressure sensor pads used by the facility are high-performance mattress sensor pads that reports a pressure level—in some cases at each of multiple points or regions on the pad. In various embodiments, these points or regions are arrayed laterally, longitudinally, in a t-shape, or in a grid relative to the supportive area of the mattress. In cases where this multipoint pressure information can be obtained from the pad, the facility uses it to detect restlessness, the probability of future fall from bed; discern nature of bed departure; duration and time in place; and assess repositioning. In some such embodiments, a circuit included in the pad enables the pad to simulate the "open or closed" behavior of a more basic pad that simply closes a circuit between two conductors if a threshold weight level is exceeded. In particular, this output processing is performed using a diode network and a transistor, which has much lower power requirements than the electrical relay that might otherwise be used.

In some embodiments, the high-performance pad incorporates a micro controller (MCU) that has one or more Analog to Digital Converters ("ADCs"). Initialization: The MCU, coming out of its reset state, starts with a clean slate and has no knowledge of past pressures. In order to initialize itself, the MCU takes a reading of the pad pressure. The following variables are then defined and all are set to the current reading:

lastReading: Working value which always contains the last known pad reading averageReading: A rolling average of the last four reading to provide data smoothing recordHigh: Upper threshold representing the lowest pressure recorded (dynamically adjusted) as calibrated by a user recordLow: Lower threshold representing the highest pressure recorded (dynamically adjusted)

Once initialized, the facility places the MCU into a sleep mode in which it wakes up on a periodic basis, such as once per 256 milliseconds.

Wake Reading and Check: On wake the MCU performs the following operations:

Perform a new pad reading and set the lastReading variable to this value

Set the averageReading=((3*lastReading)+averageReading)/4

If the lastReading is less than the recordLow then set recordLow=lastReading

This updates all variables in order to be prepped for the remaining logic. At this point, the MCU makes a decision if it has gathered enough data in order to execute the remaining logic or if it needs to go back to sleep; a newly initialized MCU will have a recordHigh=recordLow=averageReading, and if they aren't exactly equal, they are often very close in value, which creates an error condition. In this state a large enough range of pressures have not been recorded therefor an in bed or out of bed cannot be determined, which causes the system to default to the failsafe deactivated condition. In order to adapt to different responsivenesses of pad materials, a hard upper limit is set to 2% of the total range from 0 to recordHigh. This allows a signal that is slowly approaching recordHigh without even reaching it to be recaptured and encoded as an out of bed signal. This allows the dynamic calibration system to avoid endlessly adjusting to a very slowly decaying signal that manages to keep within the Transitioning region.

Region Calculation: Once the MCU has determined the recordHigh and recordLow values have diverged sufficiently, the facility executes the pressure regions logic. In this step, the MCU calculates three regions:

| Region | | Calculation | Percentage |
| --- | --- | --- | --- |
| Deactivated | High | recordHigh | 15% |
| Deactivated | Low | recordHigh − ((recordHigh-recordLow) * 0.15) | 15% |
| Transitioning | High | recordHigh − ((recordHigh-recordLow) * 0.15) | 70% |
| Transitioning | Low | recordLow + ((recordHigh-recordLow) * 0.15) | 70% |
| Activated | High | recordLow + ((recordHigh-recordLow) * 0.15) | 15% |
| Activated | Low | recordLow | 15% |

Pad State Determination: The Deactivated and Activated regions comprise the upper and lower 33% respectfully of the observed values. While averageReading is in the Activated region the pad outputs a Pad Activated signal that someone is on the pad. While averageReading is in the Deactivated region the pad outputs a Pad Deactivated signal that someone is not on the pad. The last region, Transitioning, is ignored in this step of the logic, but used later to dynamically calibrate to new conditions. Typically the averageReading travels through the Transitioning region quickly to one of the other two.

Dynamic Calibration: In an ideal situation the above stated steps would be sufficient for full pad operation. If this was the case recordHigh would be the tare weight of the mattress and recordLow would represent the weight of the patient plus mattress. During real-world usage, events sometimes occur which push the recordHigh and recordLow briefly to extremes which do not represent their intended representations. This could results from a staff member remaking a bed and accidentally leaning too hard on the mattress while tucking in the far corner. If these outlier events were not accounted for, the pad would function for a time, but could slowly become less and less reliable. In order to rectify this comment some embodiments the facility uses the Transition region calculated earlier to adjust the record values. For every wake cycle in which the averageReading is within the Transitioning region the following adjustments are made:

$$recordLow = recordLow + ((recordHigh - recordLow)/64)$$

Transitioning region is recalculated form the formulas above

This moves each record value ~1.5% of their difference towards each other, narrowing the distance between these values. If a much lower high or much high low is observed than previously these record values will start to converge until the averageReading is once again within either the Activated or Deactivated region. In some cases this convergence may take a minute, but it avoids a need for the staff to always manually intervene in the calibration process.

In some embodiments, the pad maintains a data connection to the SURE Monitor that enables calibration and region data to be transmitted to the cloud server for storage and later analysis. As this is a 2-way data connection, the cloud server is capable of sending reconfiguration commands via the monitor to the pad's MCU. This allows the formula and timings above to be reconfigured on the fly, enabling the usage of pads for special applications, such as detecting seizures or other medical or behavioral conditions.

Figure 2:
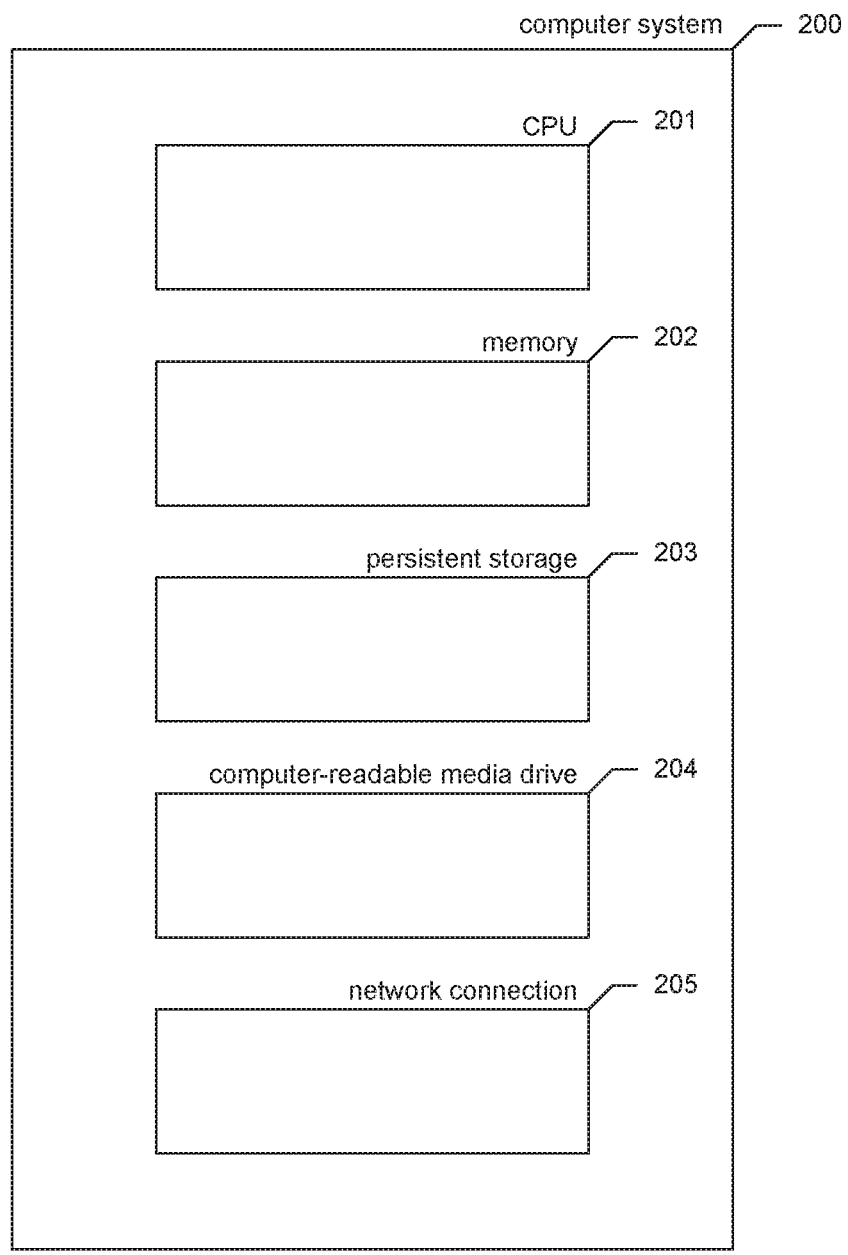
FIG. 2 is a block diagram showing some of the components typically incorporated in at least some of the computer systems and other devices on which the facility operates.

FIG. 2 is a block diagram showing some of the components typically incorporated in at least some of the computer systems and other devices on which the facility operates. In various examples, these computer systems and other devices 200 can include server computer systems, desktop computer systems, laptop computer systems, netbooks, mobile phones, personal digital assistants, televisions, cameras, automobile computers, electronic media players, etc. In various examples, the computer systems and devices include zero or more of each of the following: a central processing unit ("CPU") 201 for executing computer programs; a computer memory 202 for storing programs and data while they are being used, including the facility and associated data, an operating system including a kernel, and device drivers; a persistent storage device 203, such as a hard drive or flash drive for persistently storing programs and data; a computer-readable media drive 204, such as a floppy, CD-ROM, or DVD drive, for reading programs and data stored on a computer-readable medium; and a network connection 205 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Configurable Alarm and Warning Conditions

In some embodiments, the facility provides a mechanism that allows staff members to configure for each resident the conditions that trigger an alarm, and a warning. Examples of such conditions include entire resident weight departing bed and/or chair; partial resident weight departing bed and/or chair; weight shift in the lateral dimension in bed or in the depth dimension in a chair; or explicit alarm activation by resident; failure to depart from bed, chair, and/or toilet for more than a threshold length of time; departure from bed/chair/toilet not followed by arrival at bed/chair/toilet within a threshold length of time; departure from room or portion of room; etc.

Per Patient-Type Configurations

FIG. 3 is a user interface diagram showing a sample user interface presented by the facility in some embodiments to configure for a particular user the conditions that will trigger an alarm or warning. The user interface 300 includes information 310 identifying the resident. A staff member user can use interaction table 320 to specify warning and alarm conditions. In particular, column 321 of the table identifies events, many of which are based upon sensor output. For each event, the user can check the corresponding box in warning column 322 to incorporate that event as a warning condition for the resident. The user can similarly check the corresponding box in alarm column 323 to incorporate that event as an alarm condition for the resident. For example, it can be seen in rows 332-334 that, in the resident's bed, a weight shift or a partial departure triggers a warning, while a full departure triggers an alarm. Further, row 331 shows that explicit alarm activation events always result in alarm. Once the user has adjusted the checkboxes in columns 322 and 323 to reflect the appropriate warning alarm conditions for this resident, the user can activate submit control 390 to update the alarm and warning conditions for this resident. In some embodiments, these settings are also applied to an area of rooms in order to more efficiently and quickly setup an entire wing or unit in a health care facility with better default values.

In some embodiments, the facility permits each room, bed, or resident to be configured for various monitoring modes, such as fall monitoring, activity monitoring, combined fall and activity monitoring, or standby (monitoring disabled). For residents who are a fall risk, the fall monitoring mode alerts staff members that such a resident is standing or walking unassisted, or if sensor readings predict that they are attempting to rise to their feet. Activity monitoring mode monitors for detrimental activities and warns staff members when they occur. This can help staff members, for example, reduce the likelihood of decubitus ulcers by warning when a resident has been sitting too long, or has been lying in the same position for an extended period of time. In an independent living scenario, this same activity monitoring can be used to determine unusual resident activity such as a resident getting up in the middle of the night for a bathroom visit, but not returning to bed after 20 minutes. In a rehabilitation center, this mode can be used to notify staff of those residents who are spending too much time sitting or lying around when they should be up and about. In these scenarios, the facility uses threshold warnings in which a staff member sets a timer for either activity or lack of activity; if the timer expires, a staff member is warned. Staff can also enable a second tier warning that triggers after additional time from the first timer. For example, a staff member may set a primary timer to alert if a pressure injury patient sits for more than 2 hours. A secondary escalated warning can be set to activate at 1.1× the original timer—or 12 minutes after the 2 hours—if not attending to correctly from the first warning.

The facility also or instead permits staff members to interact with physical controls to configure a particular monitor assigned to a resident to the particular needs of that resident. For example, in some embodiments, each monitor has a set of physical controls—such as a DIP switch array inside the monitor's battery cover—that allows for the configuration of settings such as alert delay, voice playback enabled, bed/floor pad toggle, latching/nonlatching alarms, tone selection, volume level, etc. In some embodiments, the facility permits staff members to override these physical controls via a computing system, such as via web site. This can be done for individual rooms or beds, or for groups of rooms or beds. In some embodiments, the facility logs these modifications, making them traceable to the user who made the change.

Figure 4:
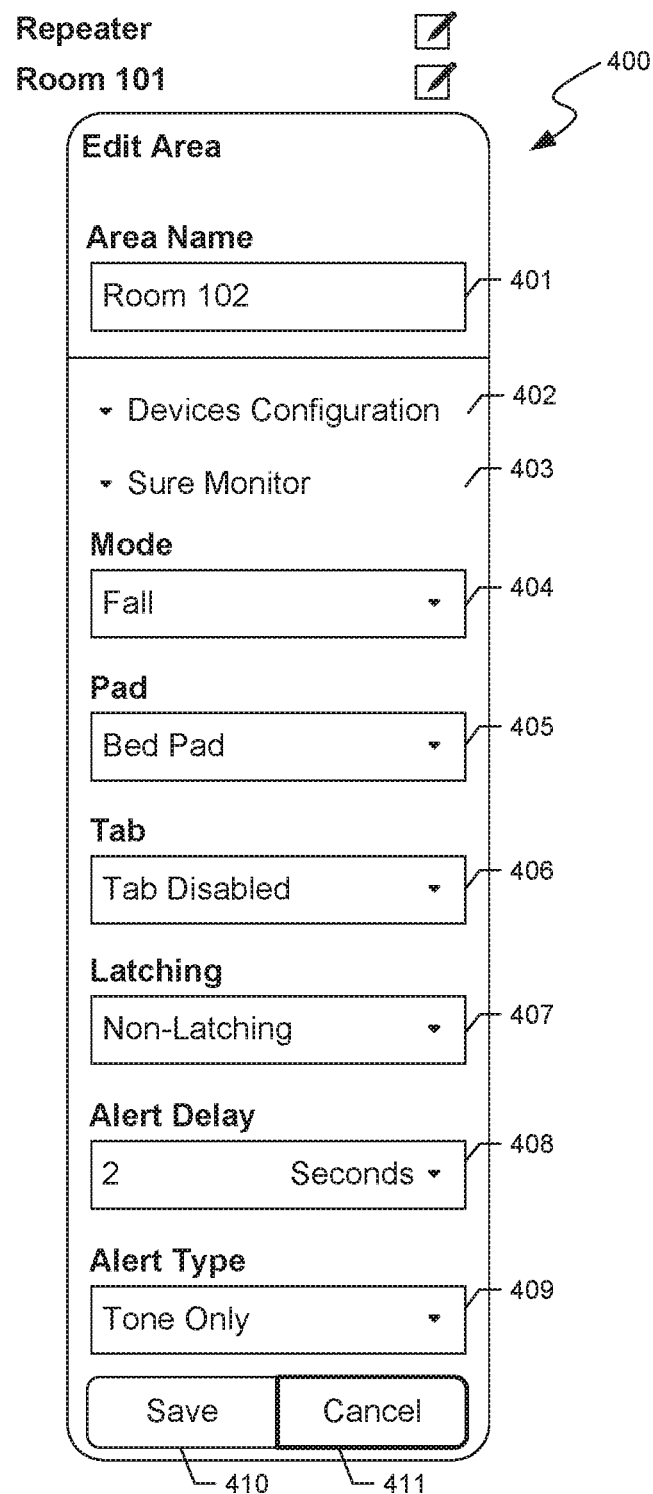
FIG. 4 is a display diagram showing a sample user interface presented by the facility in some embodiments to permit a staff member to centrally control the settings on one or more monitors.

FIG. 4 is a display diagram showing a sample user interface presented by the facility in some embodiments to permit a staff member to centrally control the settings on one or more monitors. In the user interface 400, an area name control 401 enables the user to identify an area of the health care facility whose monitors are affected by the monitor setting changes made using the user interface. The user interface further includes a devices configuration heading 402 under which device configurations can be changed. The user interface further includes a monitor heading 403 under which monitor settings can be altered. The user interface further includes control 404 that can be used to specify a mode in which the pad is to operate; in some embodiments, these include: (1) Fall Monitoring—intended for individuals classified as a fall risk by the care facility. All sensors are actively monitored for movement and recorded. Departure from a surface without a staff member's assistance, or other similar sensor indicated risky movements, will result in an alert being generated and sent to devices carried by staff members. This mode also includes the additional Activity Monitoring items below; (2) Activity Monitoring—intended for individuals not classified as a fall risk and therefor does not produce surface departure alerts to staff members. Sensor data is monitored and recorded for movement recording and trending purposes, primarily to be used to generate warnings for staff members of undesirable situations (e.g. in a chair too long which could be causing skin breakdown, detection of restless sleep, etc.). This mode can also be used to provide better individualized care as patterns can be identified which assist staff members in better times for toileting, check-ins, meals, etc.; and (3) Standby—intended to completely disable the monitoring and recording of sensor data. No alerts or warnings will be generated from this monitor. This mode allows the monitor to remain plugged in when not needed which helps maintain the integrity of the mesh data network.

The user interface further includes a pad type control 405 that can be used to specify the type of pad deployed, such as "Bed Pad," "Floor Pad," or "Chair Pad." The user interface further includes a control 406 that can be used to specify whether, for each of the monitors in the area identified by the user using the area name control, the tab is disabled; a control 407 that can be used to specify whether the alarms are latching or non-latching; a control 408 that can be used to specify a period of time before the alert is signaled; and a control 409 that can be used to specify the type of alert that is to be signaled. The user interface further includes a save control 410 to save the setting changes made using the user interface, and a cancel control 411 to cancel the setting changes made using the user interface.

Inferred Alarm and Warning Conditions

Figure 5:
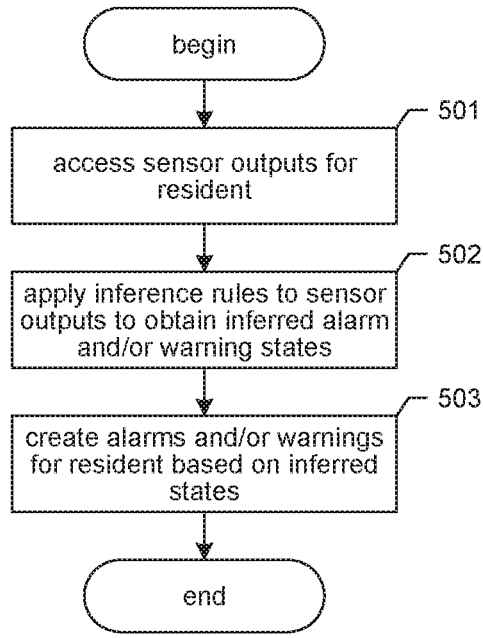
FIG. 5 is a flow diagram showing a process performed by the facility in some embodiments to automatically infer alarm states and/or warning states from data received about the resident from sensors of a variety of types.

FIG. 5 is a flow diagram showing a process performed by the facility in some embodiments to automatically infer alarm states and/or warning states from data received about the resident from sensors of a variety of types. In act 501, the facility accesses sensor outputs for the resident, such as those collected from one or more monitors by the local server. In act 502, the facility applies inference rules to sensor outputs in order to obtain inferred alarm and/or warning states. In act 503, the facility creates alarms and/or warnings for the resident based upon the states inferred in act 502. After act 503, this process concludes.

Those skilled in the art will appreciate that the acts shown in FIG. 5 and in each of the flow diagrams discussed below may be altered in a variety of ways. For example, the order of the acts may be rearranged; some acts may be performed in parallel; shown acts may be omitted, or other acts may be included; a shown act may be divided into subacts, or multiple shown acts may be combined into a single act, etc.

As one example, the facility observes a particular resident over the course of 30 days to identify the following behavioral baseline:
Resident is in bed at night 7 hours 35 minutes (±14 minutes)
Resident wake up 6 times (±1) per night.
Resident gets out of bed 2 times (±1) per night for 4 minutes (±3 minutes)

Once the facility establishes this baseline, in some embodiments it draws the following inferences from the following further observation of this resident:
Resident gets up 11 times in the middle of the night (83% increase from normal).
Resident average time in bed per night has dropped 4% night after night for 4 nights. Last night's time in bed was only 5 hours 52 minutes: infer sleep disorder, and inform nurses.
As of 2 am resident has woken up 16 times (166% increase over typical full night). Warn nurses something is keeping the resident from sleeping soundly (pain related, new medication, etc.)

Figure 6:
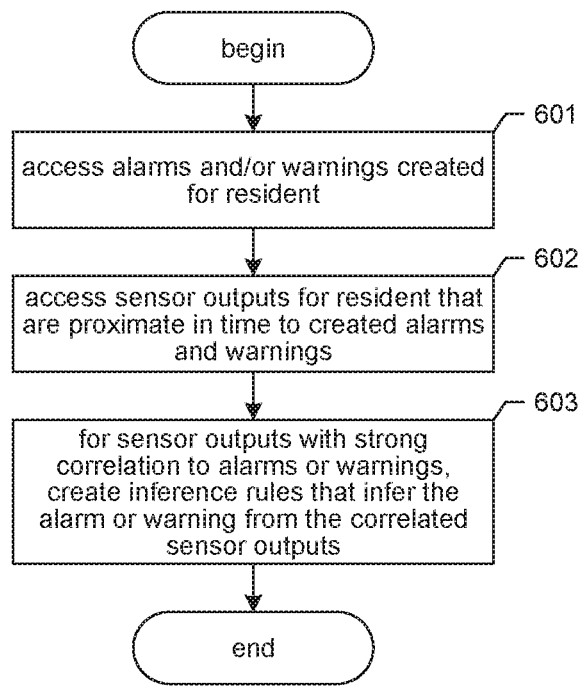
FIG. 6 is a flow diagram showing a process performed by the facility in some embodiments to use machine learning techniques to associate sensor outputs proximate in time to explicit alarms with inferred alarm states.

FIG. 6 is a flow diagram showing a process performed by the facility in some embodiments to use machine learning techniques to associate sensor outputs proximate in time to explicit alarms with inferred alarm states. In act 601, the facility accesses information about alarms and/or warnings created for a resident, such as information about alarms and/or warnings stored on the local server. In act 602, the facility accesses sensor outputs for the resident that are proximate in time to the created alarms and warnings whose information was accessed in act 601. In act 603, four sensor outputs having strong correlation to the alarms or warnings, the facility creates inference rules that infer the alarm a warning from the correlated sensor outputs. After act 603, this process concludes.

In some embodiments, the facility predicts an imminent resident need using a pattern from a single sensor over a period of time; in some embodiments, the facility uses a pattern observed among an array of sensors, including such sensors as pressure pads in beds, chairs, wheelchairs, and sofas; door contact sensors on exterior doors, bedroom door, and bathroom door; and motion sensors in major travel areas.

An example of using patterns in data from a single sensor to predict imminent resident need involves a multiple-zone bed pressure pad sensor, which can detect where a patient is in the bed and how they are moving around. This sensor splits the width of the bed into section with each section reporting its relative pressure. By observing the pattern of the data from these sections, the facility makes predictions for a patient getting into bed, restlessness, turning or lack thereof, and movement indicative of imminent bed exit as follows:

1. Gets into bed from the right side sitting on the edge.

2. Lays down into the middle of the bed.
3. Rolls to the far left side of the bed.
4. Rolls back to the middle and begins to fidget
5. Exits the bed on the right side Between events 4 and 5, the facility uses prior patterns of observations to predict the resident's exit, and alerts staff members to attend to the resident.

In some embodiments, the facility is used in conjunction with a process for issuing visitor badges to visitors. In various embodiments, this badge-issuing process is automatic, semi-automatic, or manual. According to the process, when a visitor arrives to visit a particular resident, the resident and visitor's identity are recorded, together with the arrival time. The visitor is issued a badge that visually identifies the visitor, including in some cases an identification of the resident being visited, the arrival time, visitor's name, visitor's photo, etc. In some embodiments, the badge or a holder in which the badge is placed contains a tracking mechanism, such as an RFID beacon, a Bluetooth low energy beacon, etc.

In some embodiments, the facility identifies some or all of the sensor outputs for the visited resident during the visit period that are to be ignored for purposes of generating an alarm; that are to be ignored for purposes of identifying resident behavior patterns; or both. In some embodiments, the facility identifies this period based upon the presence of the tracking device in the patient's room, near the patient's bed, etc. In some embodiments, the facility assumes that the visit will last a predetermined amount of time after the visitor's arrival, such as two hours. In some embodiments, the process prompts or requires the visitor to check out on exit, and the period is ended at this time. In some embodiments, the facility ignores all sensor outputs during the period for one or both purposes. In some embodiments, the facility automatically identifies a proper subset of the sensor outputs during the period to ignore based on, for example, the specific location and/or movement patterns of the badge beacon; the typical behavior patterns of the resident; observations made by staff members about where the visitor is in the room at certain points; etc.

Silent Dispatch

In some embodiments, the facility responds to an alarm or warning condition, such as a departure from bed, in a way that summons a staff member without creating a sensory disturbance for that resident, or for other people nearby, such as by selectively prompting staff members using portable devices carried by them. In some such embodiments, the facility uses portable devices carried by staff members—such as smartphones—to selectively prompt a certain staff member to attend to the resident who is the subject of the alarm. In some cases, the facility uses a set of rules to select the staff member who is initially prompted, such as by selecting a staff member assigned directly to the resident; a staff member assigned to a physical area where the resident is located, or in which the resident is assigned to reside; a staff member who is assigned to a certain type of activity; a staff member whose present location is nearest the resident; and/or a staff member who has gone the longest since handling a tracked action. If the prompted staff member is available to attend to the alarm, s/he can use his or her portable device to accept the alarm. If the prompted staff member does not accept the alarm, one or more additional staff members are summoned. In some embodiments, the facility provides a mechanism that allows staff members to configure for each resident which staff members are summoned for alarms raised for the resident, in some cases differently based on the type of the alarm.

In some embodiments, a health care facility organizes its staff using a tree hierarchy of nested areas. The top of this tree is a single health care facility whose children are defined by the organizational strategy of the health care facility in question. For example, in a tree in particular a health care facility, the root mode may have four child nodes called wings, each wing having two child nodes called units, each unit node having four child nodes called bays, and each bay node having child nodes called beds. In a simpler instance, a tree health care facility includes a six root node having units as child nodes, each of those unit nodes having rooms as child nodes. This hierarchy of areas allows the device to be assigned at the lowest level-such as rooms—and staff members to be assigned at any level in the hierarchy.

Utilizing the nested area hierarchy defined above, when an alert is generated at a device, the facility assigns that alert to the area associated with the device. The facility then begins to look for staff members assigned to that area in order to dispatch a request for action. If no staff members are found assigned to that area the area's parent in the hierarchy is found and the notification system proceeds in a similar manner. If this parent area also has no staff members assigned its parent is then found and the process continues until all levels of the hierarchy are exhausted or somebody is able to address the alarm. In addition to walking up this escalation hierarchy, in some embodiments the facility also uses a three tier system of responder levels. Each staff member is assigned a responder level by their administration. In a typical scenario, staff members on the floor responding to alarms are assigned as a first level responder. Unit managers or managers of the floor staff would be assigned as second level responders. The Director of Nursing or health care facility wide administrator would be assigned as a third level responder.

In some embodiments, the facility walks up the area hierarchy but for each step it also progresses through the responder levels from first to second to third. This allows upper management to only be notified of an alarm if lower level staff have not responded appropriately.

The facility typically relies upon the currently logged in users, the devices they are using to connect, and the connectivity status of those devices. In some embodiments, only those staff members who are logged in and activity connected will be included in the alert escalation system described above.

In some embodiments, each logged in device checks in with the servers every 60 seconds. If a device does not check in for 2 minutes, the facility removes the device and the user logged into that device from the list of staff members available for responding to an alarm. This typically happens if the device is moved out of Wi-Fi range, but can also occur due to an Internet outage, an empty device battery, or someone turning the device off without logging out. As soon as the device resumes its 60 second check-ins, the device and user are returned to the list of available staff members without requiring the user to reauthenticate.

In the event that no staff members are available to receive an alert (whether due to lack of logins, or all logged in staff members being busy), the facility will not have the means to silently call for help on behalf of the resident. In this scenario, the facility triggers a failsafe mechanism, signaling the monitor in the room to ignore the silent mode selection and begin to audibly alarm in an attempt to get the attention of the physically closest staff.

In some embodiments, in the event that no staff members are available to receive an alert, the health care facility administrator can be configured to receive emails, text messages, and/or phone calls. This can help notify health care facility administration that something is amiss at the location.

Figure 7:
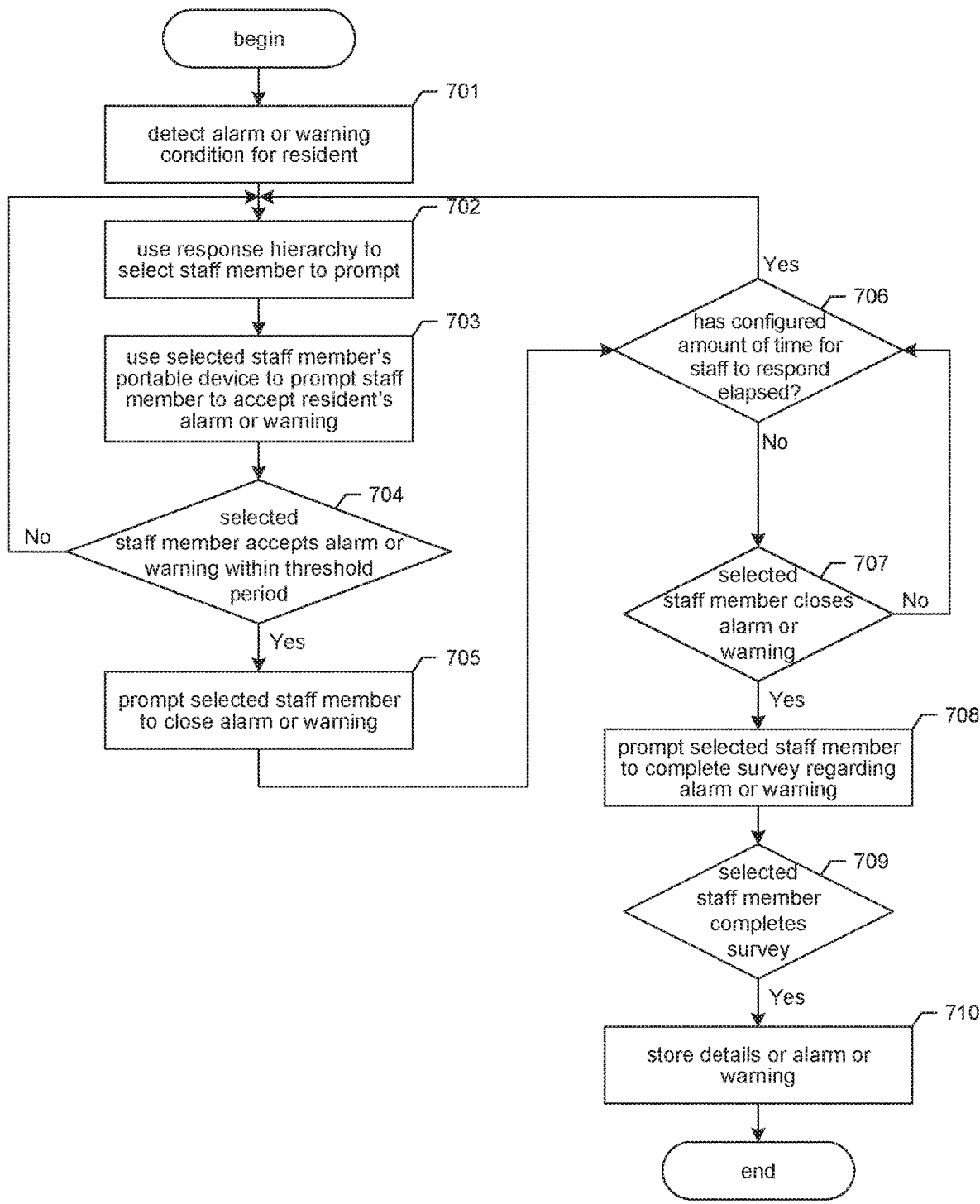
FIG. 7 is a flow diagram showing a process performed by the facility in some embodiments to perform silent dispatch of a staff member in response to a resident alarm or warning.

FIG. 7 is a flow diagram showing a process performed by the facility in some embodiments to perform silent dispatch of a staff member in response to a resident alarm or warning. In act 701, the facility detects an alarm or warning condition for a resident. In act 702, the facility uses a response hierarchy, or other rules, to select a staff member to prompt to accept and respond to the alarm or warning. In act 703, the facility uses a portable device of the selected staff member to prompt this staff member to accept the resident's alarm warning. In act 704, if the staff member selected in act 703 accepts the alarm or warning within a threshold period of time, such as 30 seconds, then the facility continues in act 705, else the facility continues in act 702 to select another staff member to prompt.

In act 705, the facility prompts the selected staff member to close the alarm or warning once the staff member has checked on the resident and resolved any matters of concern. In act 706, if a configured amount of time for the prompted staff member to respond has elapsed since prompting, then the facility continues in act 702, else the facility continues in act 707. In act 707, if the selected staff member closes the alarm or warning, then the facility continues in act 708, else the facility continues in act 706. In act 708, the facility prompts the selected staff member to complete a survey regarding the alarm or warning and its resolution. In act 709, when the selected staff member completes such a survey, the facility continues in act 710. In some embodiments, the facility continues in act 710 even where no survey is completed. In act 710, the facility stores details of the alarm warning for later reference and/or analysis. After act 701, this process concludes.

FIG. 8 is a user interface diagram showing a sample user interface presented by the facility in some embodiments to allow a staff member user to specify a hierarchy among the staff for prompting staff members to respond to resident alarms and warnings. User interface 800 identifies several groups of one or more staff members 811-819. For each of these groups, the user may enter a number indicating the precedence of this group in the staff prompting cycle for an alarm or warning. Based upon the numbers shown in the drawing, when an alarm warning occurs, the nursing assistant on duty who is assigned to the resident is prompted first. If this nursing assistant affirmatively declines or fails to accept during the threshold amount of time, then the facility prompts the nearest nursing assistant, and then other nearby nursing assistants, and so on.

FIG. 9 is a user interface diagram showing a sample user interface presented by the facility in some embodiments to prompt a staff member to respond to an alarm. The user interface 900 includes a prominent indication 910 that the staff members being prompted about a resident alarm. Information 920 identifies the resident and/or area who is the subject of the alarm, and her location. Indications 931-932 reflect the type of the alarm, and the time at which it was raised. The staff member may activate control 941 to accept the alarm, or activate control 942 to decline the alarm. If the staff member does neither for the threshold amount of time, in some embodiments the facility removes the prompt from the display, as the prompt is at this time reassigned by the facility to a different staff member.

Post-Alarm Survey

In some embodiments, after a staff member accepts the alarm, the facility conducts a survey with the staff member to collect information about the alarm and its resolution. In some embodiments, the facility stores the collected information for further analysis, such as to identify physical hazards that lead to frequent falls, assess response time and other staff performance metrics; infer information about the resident such as bathroom frequency/schedule; referral suggestions in light of observed resident information; etc.

In some embodiments, after a staff member declines an alarm, that staff member is marked a busy for the next several minutes. Staff members who accept an alarm are also marked as busy until the alarm they accepted is resolved. This allows subsequent alarms to skip these staff members so that they can complete whatever task they are activity working on with fewer interruptions. This also speeds the process of alarm escalation by targeting staff members most likely to be available to respond.

FIGS. 10A-10E are user interface diagrams showing a sample user interface presented by the facility in some embodiments to collect information about a resident alarm or warning and its resolution from the staff member who responded to the alarm or warning. FIG. 10A shows a first display 1010 containing a question about why the resident left their bed or chair. The staff member user can select any of reasons 1011-1016, which are configurable by the health care facility. In response, the facility transitions to a second display of the user interface.

FIG. 10B shows the second display 1020 containing a question about whether the resident fell to the floor. The user can select a positive response 1021 or negative response 1022. In response, the facility transitions to a third display of the user interface.

FIG. 10C shows the third display 1030 containing a question about the reason for the fall. The user can select any of reasons 1031-1036, or may enter another reason into box 1037 and activate control 1038. In response, the facility transitions to a fourth display of the user interface.

FIG. 10D shows the fourth display 1040 containing a question about whether the resident was injured when s/he fell. The user can select a positive response 1041 or negative response and 42. In response, the facility transitions to a fifth display of the user interface.

FIG. 10E shows the fifth display 1050 containing a summary of the responses to the survey's questions. If the listed information is accurate, the user can activate a submit control 1051 in order to complete the survey. If any information is inaccurate, the user can activate a back control 1052 to revise his or her responses.

Per-Patient Alarm Attributes

In some embodiments, the facility provides a mechanism that allows staff members to configure alarm attributes for each resident. Examples of such attributes are silent/audible; visible/non-visible; volume level; duration; sound type; speech/non-speech; etc.

Figure 11:
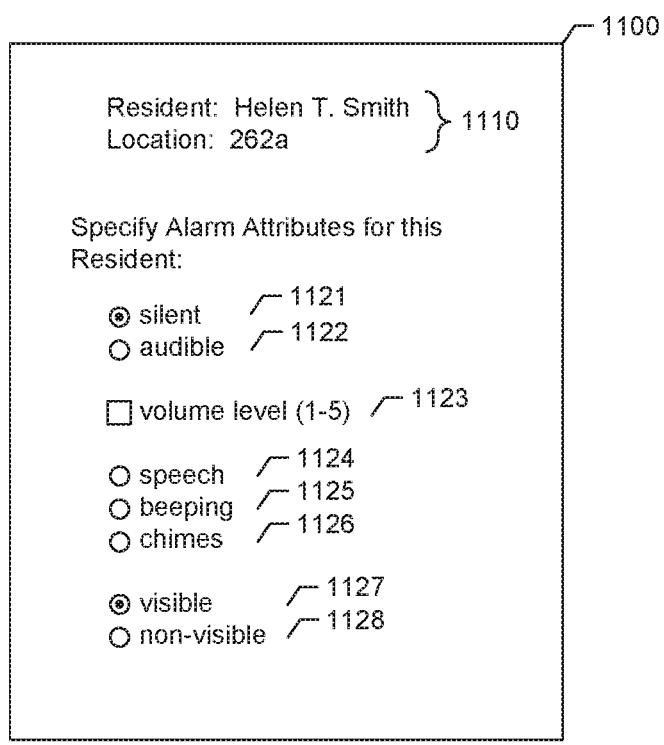
FIG. 11 is a user interface diagram showing a sample user interface provided by the facility in some embodiments to enable staff member user to configure alarm attributes for a particular resident.

FIG. 11 is a user interface diagram showing a sample user interface provided by the facility in some embodiments to enable staff member user to configure alarm attributes for a particular resident. The user interface 1100 includes identifying and location information 1110 for the resident. It further lists alarm attributes 1121-1128, which the user may select for the user. For example, as shown, silent alarms are selected for this resident, and visible alarms are also selected.

Timeline View of Alarms

In some embodiments, the facility provides a visual user interface that shows the alarms (or warnings, or alarms and warnings) that have occurred over time relative to a timeline. In various embodiments, these are for a single, selected resident; a group of residents, such as those who reside in a particular area of the health care facility, or are in a particular category of residents based on, for example, their care needs; or all of the residents in the health care facility. In some cases, certain types of alarms (and/or warnings) are shown in their own color or pattern. In some embodiments, a staff member can click on a point in the timeline view to display additional detail about the alarms and warnings to which that point relates.

Figure 12:
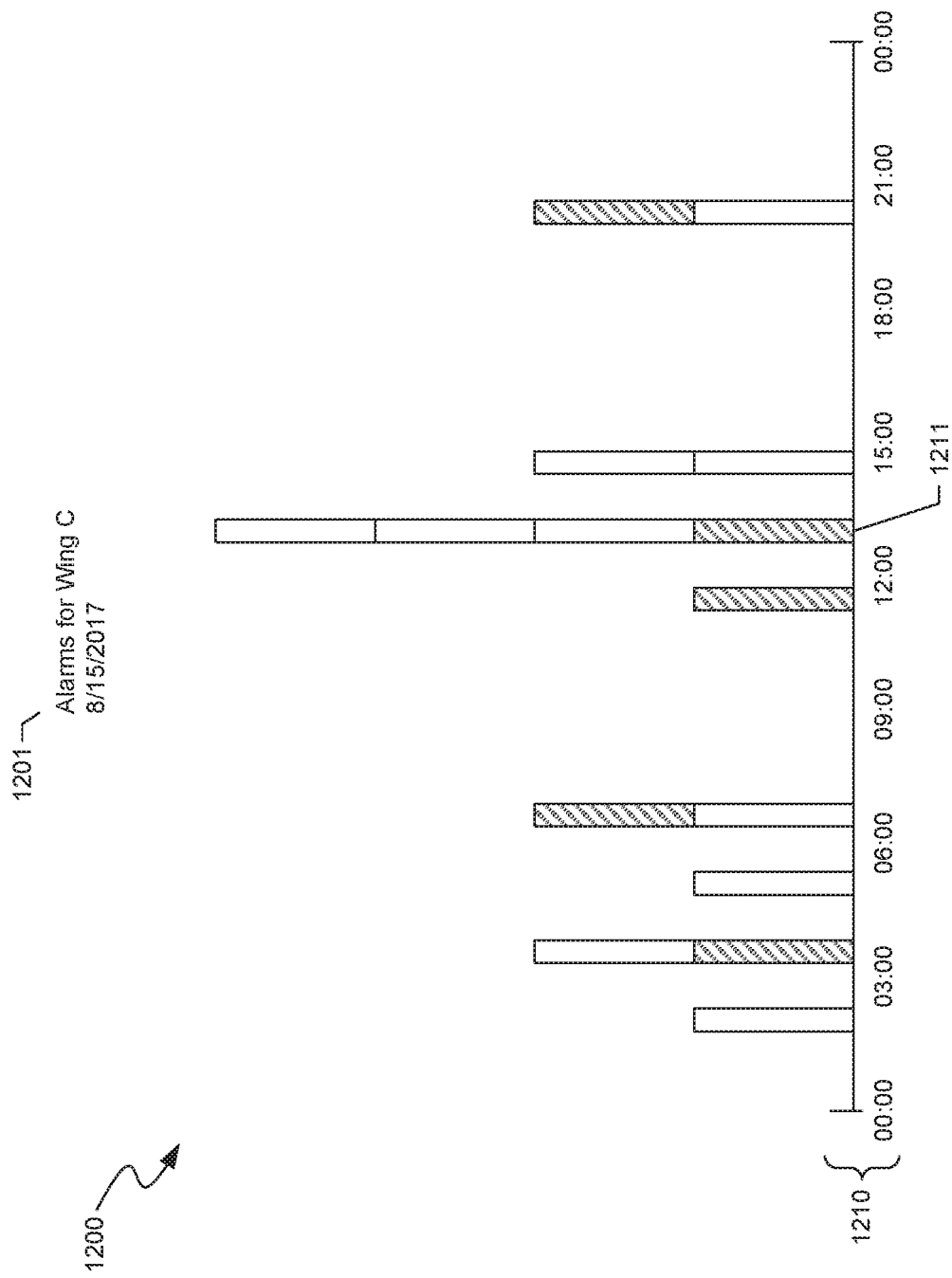
FIG. 12 is a user interface diagram showing a sample user interface provided by the facility in some embodiments to show the timing of alarms and/or warnings in a particular care facility or area of a care facility.

FIG. 12 is a user interface diagram showing a sample user interface provided by the facility in some embodiments to show the timing of alarms and/or warnings in a particular health care facility or area of a health care facility. The user interface 1200 includes a heading 1201 indicating that the user interface shows the timing of alarms that occurred in a "Wing C" area of a health care facility on Aug. 15, 2017. The user interface shows a timeline 1210 representing the span of time during that day, and contains stacks of rectangles such as stack 1211 at various points on the timeline showing alarms that occurred at that time. Taller stack reflect larger numbers of alarms at the same time. In some embodiments, the facility causes certain rectangles to have colors, patterns, etc. reflecting different alarm attributes, such as alarm type, alarm resolution type, alarm resolution time, alarm versus warning, etc. In some embodiments, the user can select a rectangle or stack rectangles to display more detailed information about the corresponding alarm or group of alarms.

Figure 13:
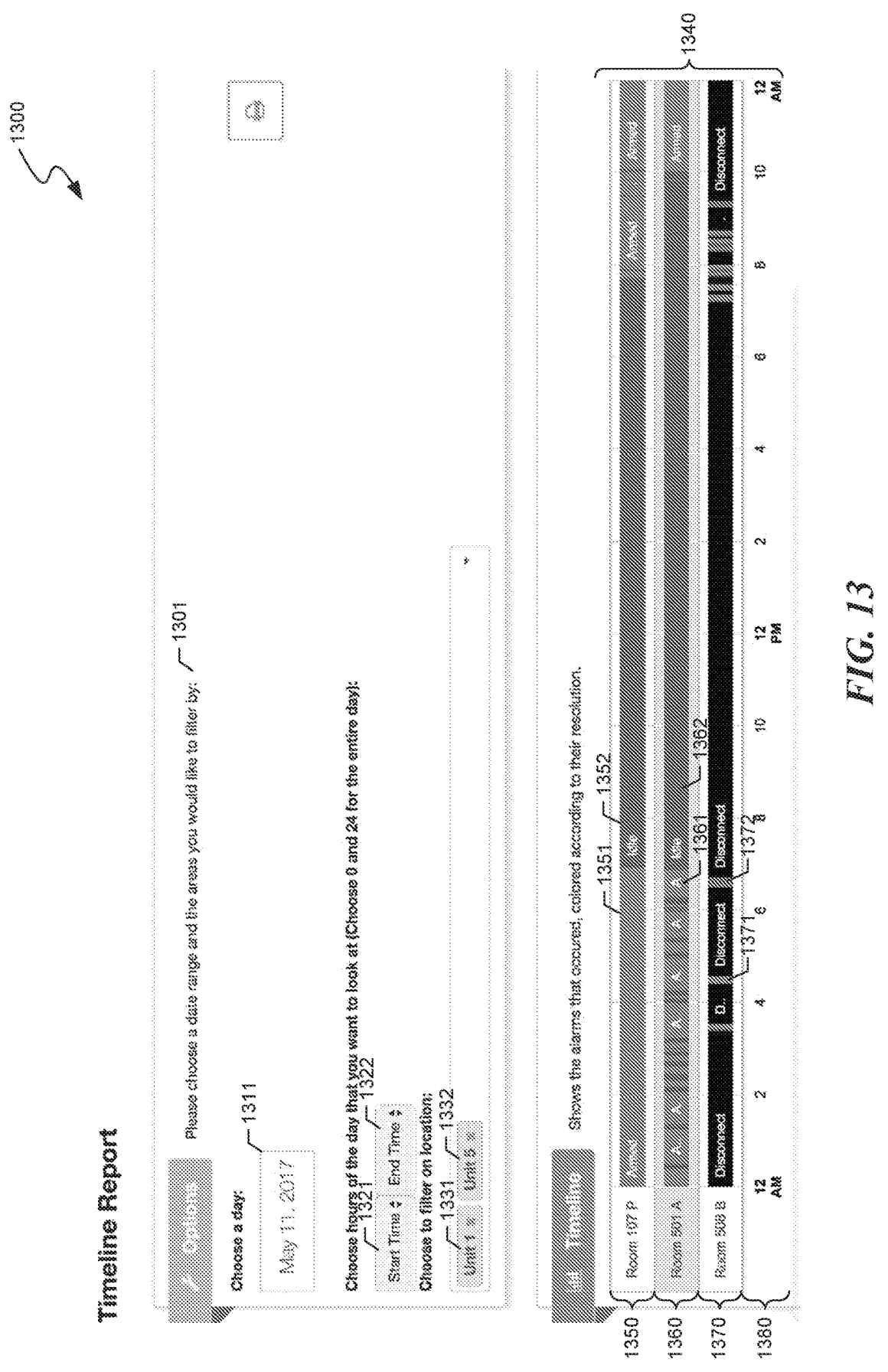

FIG. 13 is a user interface diagram showing a second sample user interface provided by the facility in some embodiments to show the timing of alarms, warnings, and special or other types of events that occur in a particular health care facility or area of a health care facility. The user interface 1300 shows a per-room timeline view reflecting what occurs in each of multiple rooms over the course of a period of time, such as a day. Timeline 1350 for the resident in room 107P shows that this resident had a very restful morning with no interruptions, and woke about 7:30 a.m. On the other hand, timeline 1360 for the resident in room 501A shows that this resident had a very restless night with many sleep interruptions, many of which are accompanied by bed exists that lasted several minutes before returning to bed. Timeline 1370 shows activity in room 508B, which is having sensor hardware or sensor network issues, as it has not maintained a reliable data connection for the majority of the day shown. In some embodiments, in response, the facility generates a trigger for staff to investigate this issue.

Figure 14:
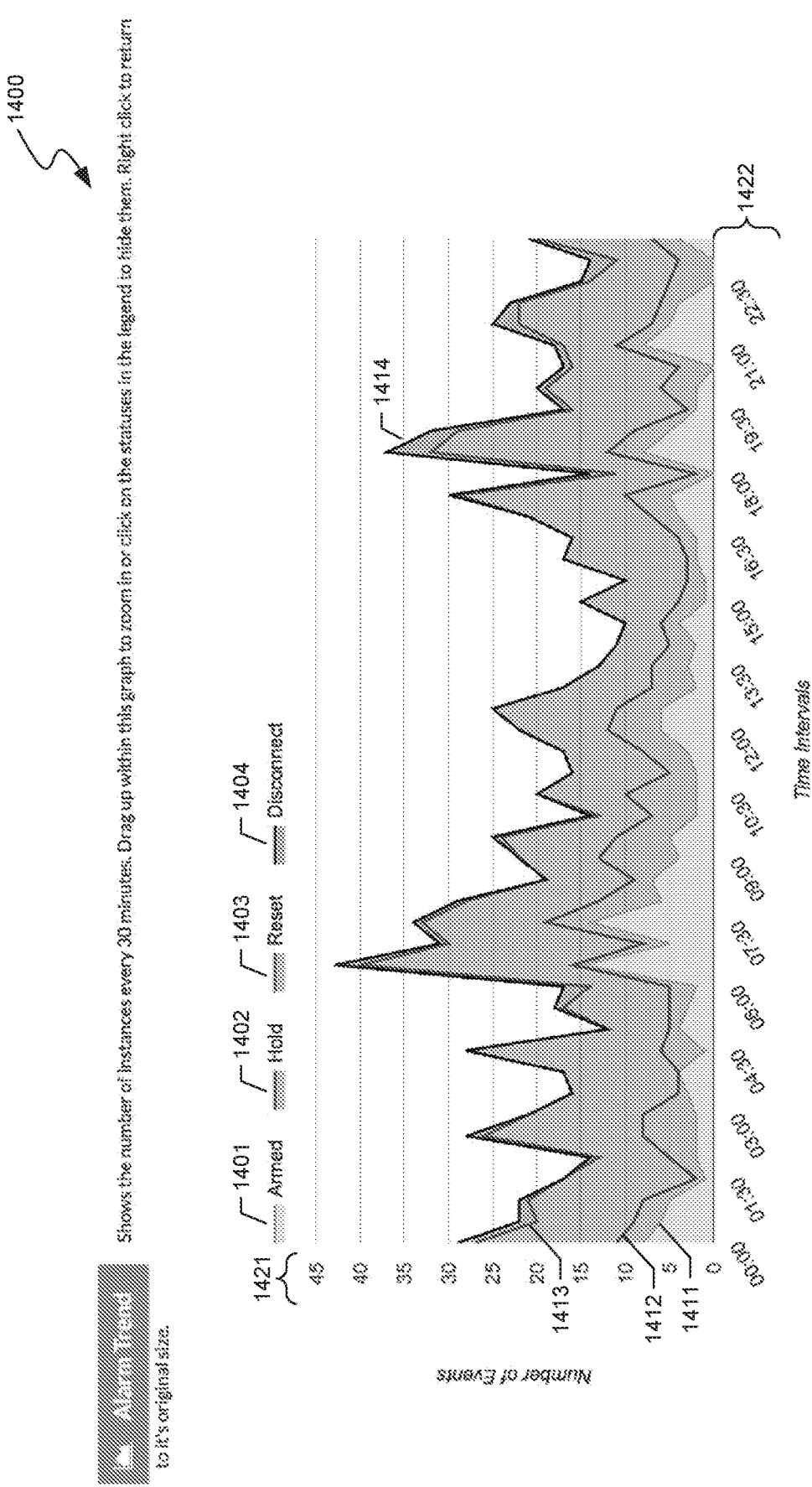
FIG. 14 is a user interface diagram showing a third sample user interface provided by the facility in some embodiments to show the timing of alarms, warnings, and special or other events in a particular care facility or area of a care facility.

FIG. 14 is a user interface diagram showing a third sample user interface provided by the facility in some embodiments to show the timing of alarms, warnings, and special or other events in a particular health care facility or area of a health care facility. In user interface 1400, events are aggregated across a group of rooms, such as all of the rooms in a health care facility, across the course of a day. This can be effective to identify peak time of the day for alerts, and determining what number of these were attended by staff as opposed to residents returning to a bed or chair on their own.

Resident Behavior Cues

In some embodiments, the facility provides a mechanism that allows staff members to configure voice behavior cues for each resident to suggest actions to him or her, such as "wait by the bed" or "use your walker."

Figure 15:
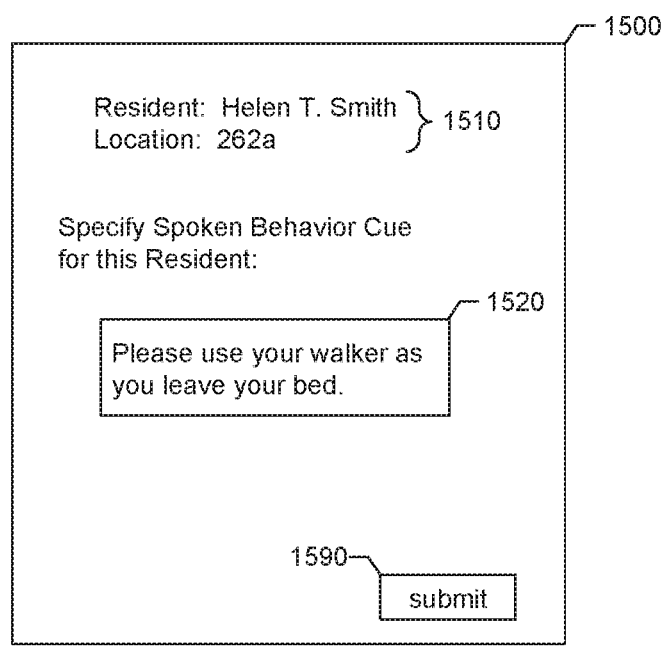
FIG. 15 is a displayed diagram showing a display presented by the facility in some examples to reflect storage of the second user's annotations.

FIG. 15 is a user interface diagram showing a sample user interface provided by the facility some embodiments to enable a staff member user to configure a voice behavior Q4 particular resident. User interface 1500 includes information 1510 identifying the resident and her location. It further includes a field 1520 into which the user can enter a voice behavior cue to be issued to the resident in certain circumstances, such as when she departs her bed. In some embodiments, the facility uses a text-to-speech capability of the monitor device to output this voice cue to the resident. In some embodiments (not shown), a particular resident's monitor device stores passages of speech recorded specifically for this resident, such as by a relative of the resident. In such embodiment, this user interface shows a summary or transcription of each of these passages, and allows the user to select among them. After specifying the voice cue for the resident, the user activates a submit control 1590 in order to complete the configuration.

Patient and Staff Member Location Tracking

In some embodiments, the facility tracks the physical location of some or more residents, such as by performing trilateration with respect to a radio beacon broadcast by a transmitter embodied in an object worn by a resident, such as using radio receivers such as those incorporated into monitor devices. In some embodiments, the facility also uses radio repeaters for this purpose. In some embodiments, the facility recurringly compares each resident's location to regions of the health care facility in which the resident should or should not be present, and uses the results of these comparisons to generate alarms or warnings where the resident has departed a region in which s/he should be present or is on a path to do so, and/or where the resident has entered a region in which s/he should not be present or is on a path to do so.

Some devices move about the health care facility, including wheelchair fall monitors installed in wheelchairs, and call pendants worn around the neck of residents. Because these devices are mobile they are not assigned to a static location within the health care facility's location hierarchy. Some embodiment, the facility identifies the location of these devices using the wireless radios contained inside of them. When an alarm is generated, the data is sent to the server for processing and a local radio broadcast is sent to all mesh devices in the immediate area in order to determine approximate distances. The associated statically-assigned device ids and approximate distances are then sent to the server where an algorithm determines the approximate location of the alarming device using trilateration or weighted average calculations. This estimated location is then correlated to the health care facility map to determine which nested area it is contained within. This allows the system to notify staff members in the immediate vicinity of the alarm instead of sending the message to where the device was originally provisioned. This also provides a marker on the health care facility map to aid staff members in quickly location the alarm.

In some embodiments, any fall monitor can be configured into either a mobile or fixed mode. In the mobile mode, the position of the monitor can be determined with respect to monitors that are in the fixed mode. In some embodiments, the mode is selected manually by staff members. In some embodiments, each monitor infers its mode using one or more of a variety of approaches, including such approaches as using an accelerometer incorporated into the monitor, determining whether the monitor is changing position with respect to most or all of the other monitors it can observe; whether the device is battery- or wall-powered; etc.

In some embodiments, the facility periodically locates each monitor, call pendant, and other devices used for tracking as a basis for maintaining and/or recording the location of these objects over time.

In some embodiments, the facility uses a trilateralation process to determine this approximate location. Trilateration is a geometric process of determining absolute or relative locations of points by measurement of distances, using the geometry of circles, spheres or triangles. In addition to its interest as a geometric problem, trilateration does have practical applications in surveying and navigation, including global positioning systems (GPS). In contrast to triangulation, it does not involve the measurement of angles. In two-dimensional geometry, it is known that if a point lies on two circles, then the circle centers and the two radii provide sufficient information to narrow the possible locations down to two. Additional information may narrow the possibilities down to one unique location. The facility uses each room's monitor as a center point of a circle to determine the location of the roaming device (e.g., wheelchair or pendant). The "measurement of distances" happens using the Received Signal Strength Index ("RSSI") of the wireless radio signal from the surrounding rooms' monitors.

Figure 16A:
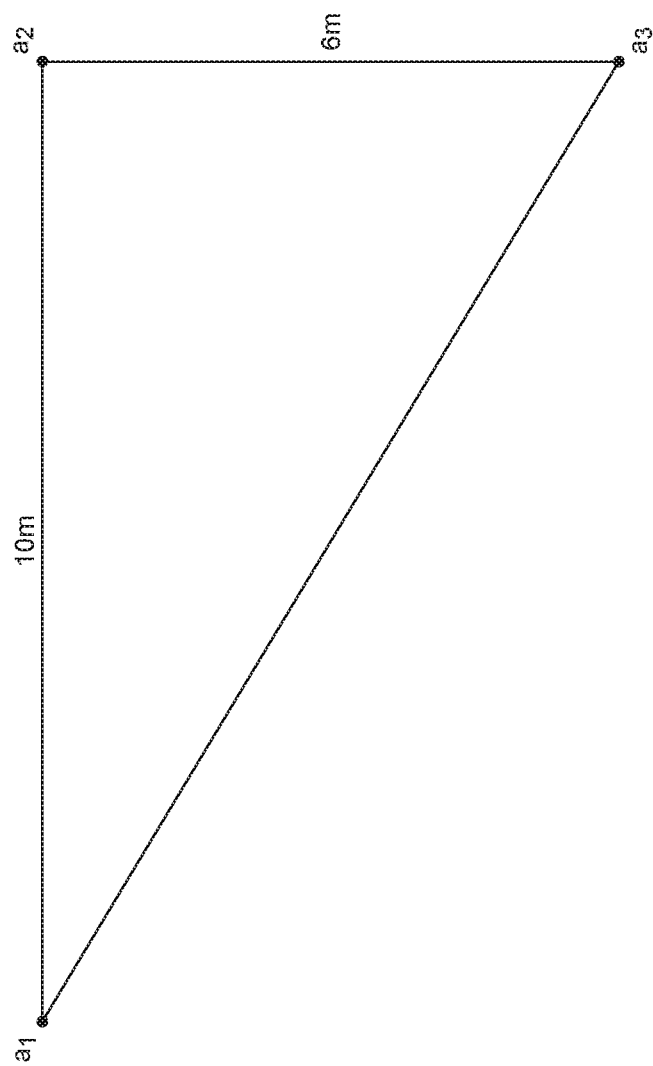
FIGS. 16A-16F are diagrams showing an additional form of device location-finding used by the facility in some embodiments.

FIGS. 16A-16F are diagrams showing an additional form of device location-finding used by the facility in some embodiments. FIG. 16A shows the locations of three fixed location finding points within the health care facility, such as points in which there are fall monitors operating in fixed mode. These locations are shown as points $a_1$, $a_2$, and $a_3$. In some embodiments, these points correspond to the known locations of three fall monitors nearest the tracked device, i.e., those that are receiving the strongest signals transmitted by the tracked device.

Figure 16B:
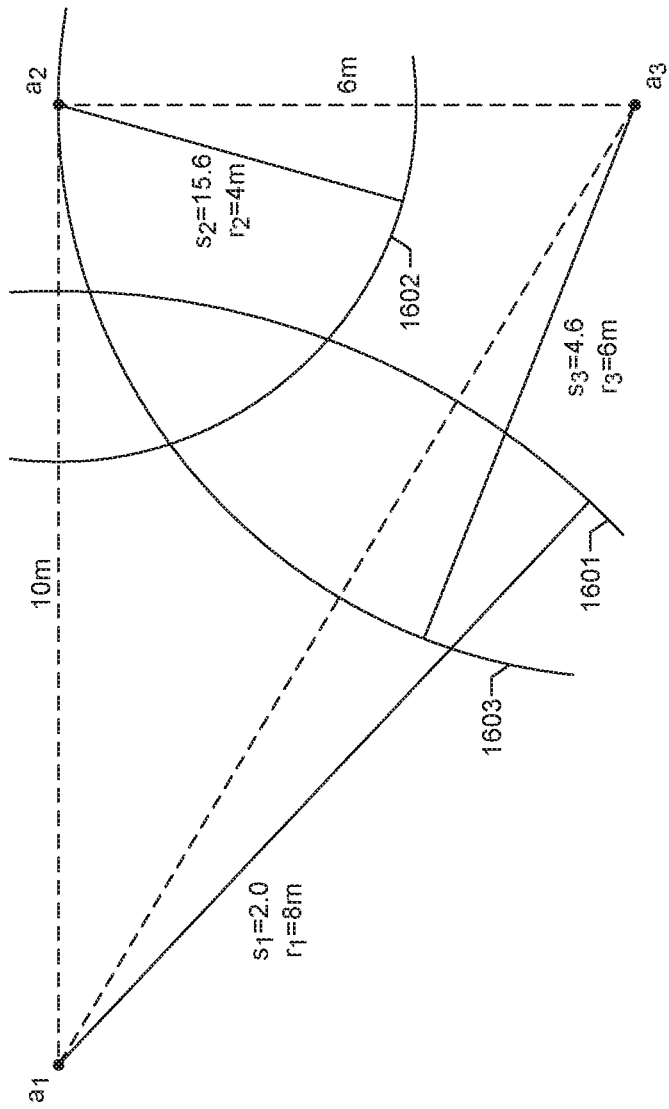

FIG. 16B shows a first step of range-finding between the tracked device and each of the fixed fall monitors. With respect to fall monitor $a_1$, it can be seen that this fall monitor observes a signal strength $s_1$ of 2.0 from the tracked device, which the facility converts to an estimated radius $r_1$ of 8 meters. Thus, the facility describes a first arc 1601 corresponding to this radius about point $a_1$. Similarly, the facility determines a signal strength $s_2$ of 15.6 and an estimated radius $r_2$ of 4 meters for point $a_2$, causing it to describe arc 1602 about point $a_2$. Finally, the facility determines a signal strength $s_3$ of 4.6 and a corresponding estimated radius $r_3$ of 6 meters for point $a_3$, causing it to describe arc 1603 about point $a_3$.

Figure 16C:
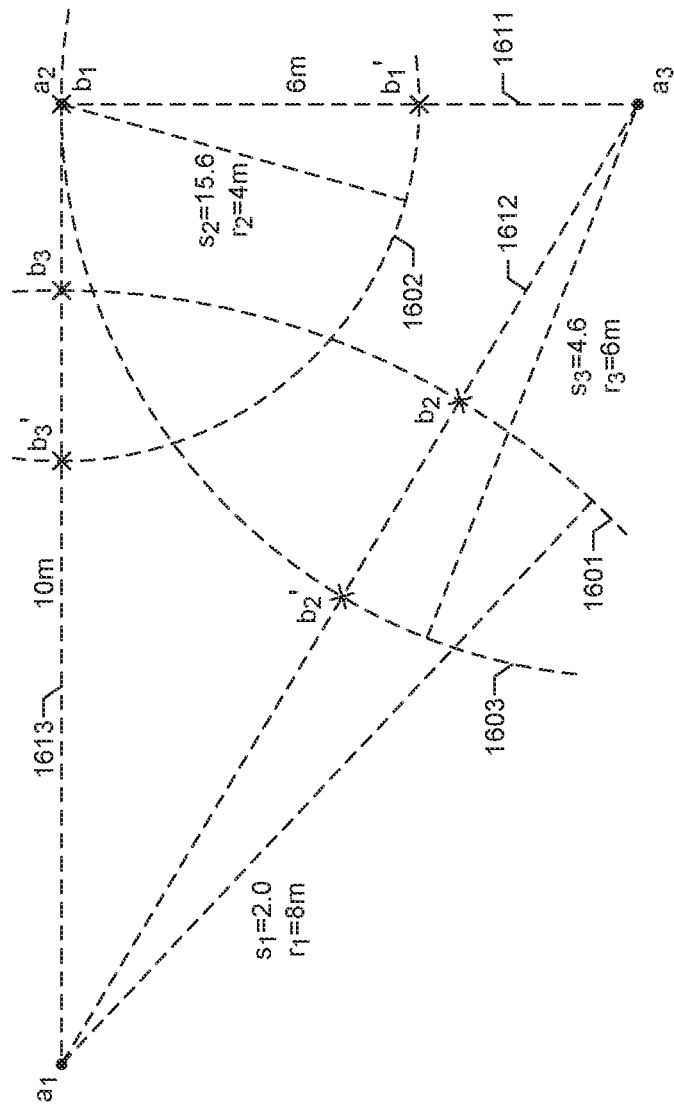

FIG. 16C shows the identification of intersection points using the described arcs. For each pair of points among the three points, the facility describes a line containing these two points. For example, between points $a_1$ and $a_2$, the facility describes line 1613. On each of these lines, the facility identifies the two points at which an arc having one of these two points as its center intersects the line. For example, considering the line defined by points $a_1$ and $a_2$, it is intersected by arc 1601 at point $b_3$, and by arc 1602 at point $b_3'$.

Figure 16D:
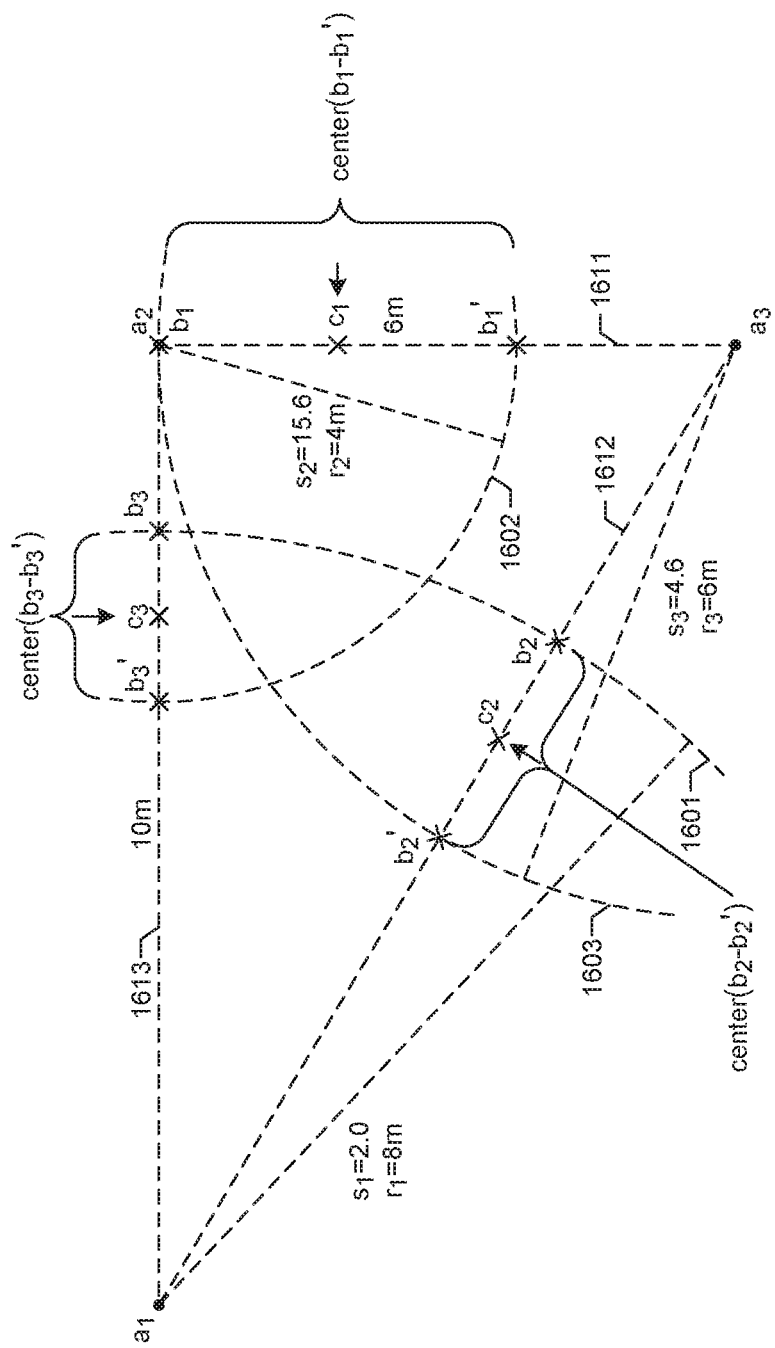

FIG. 16D shows the process of identifying the midpoint between a pair of points identified in FIG. 16C on each of the sides of the triangle. It can be seen that the facility identifies point $c_1$ as the midpoint of segment $b_1$-$b_1'$; identifies point $c_2$ as the midpoint of segment $b_2$-$b_2'$; and identifies point $c_3$ as the midpoint of segment $b_3$-$b_3'$.

Figure 16E:
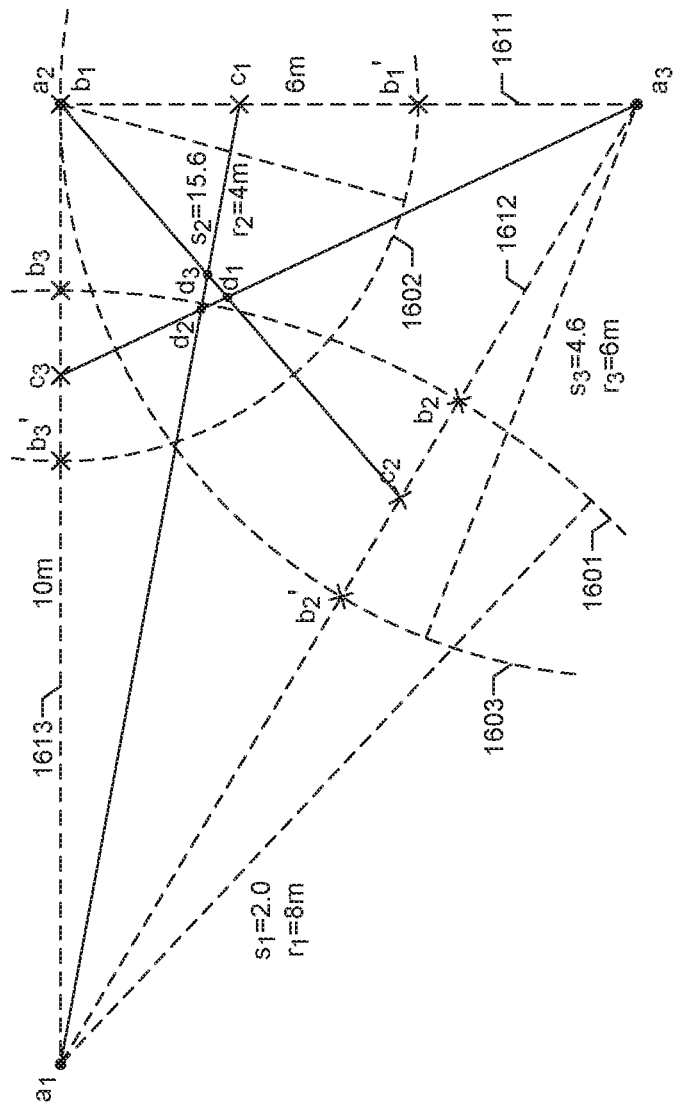

FIG. 16E shows the determination of another triangle. The facility describes triangle $d_1$-$d_2$-$d_3$ by connecting $a_1$ to $c_1$, $a_2$ to $c_2$, and $a_3$ to $c_3$.

Figure 16F:
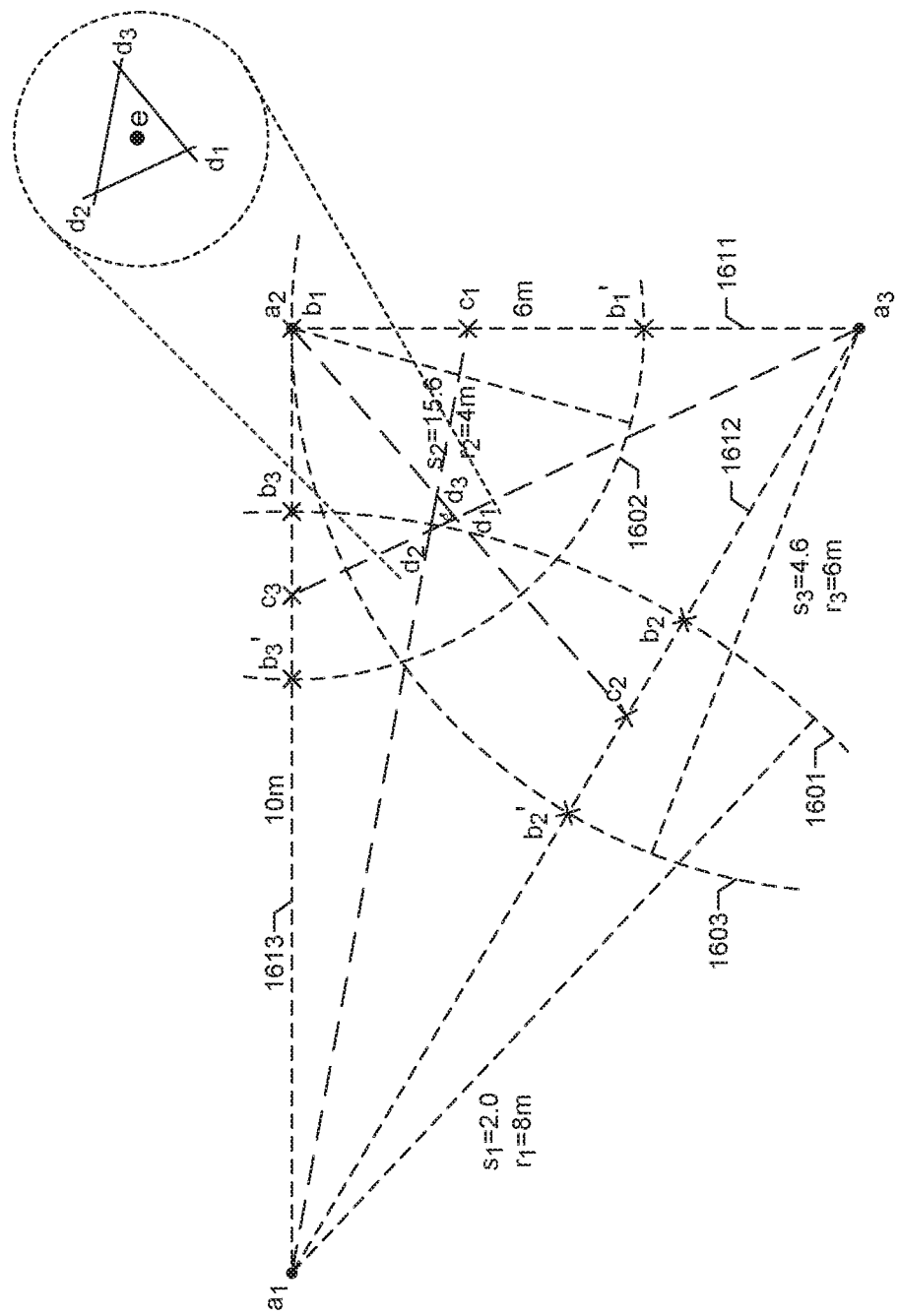

FIG. 16F shows the determination of the center point e for triangle $d_1$-$d_2$-$d_3$. In some embodiments, the facility determines the center of this triangle as its center of gravity, or "centroid." In some embodiments, the facility determines the center by averaging the north-south location of each of the vertices, and averaging the east-west location of each of the vertices. Based upon this processing, the facility estimates the location of the tracked device as point e.

Figure 17:
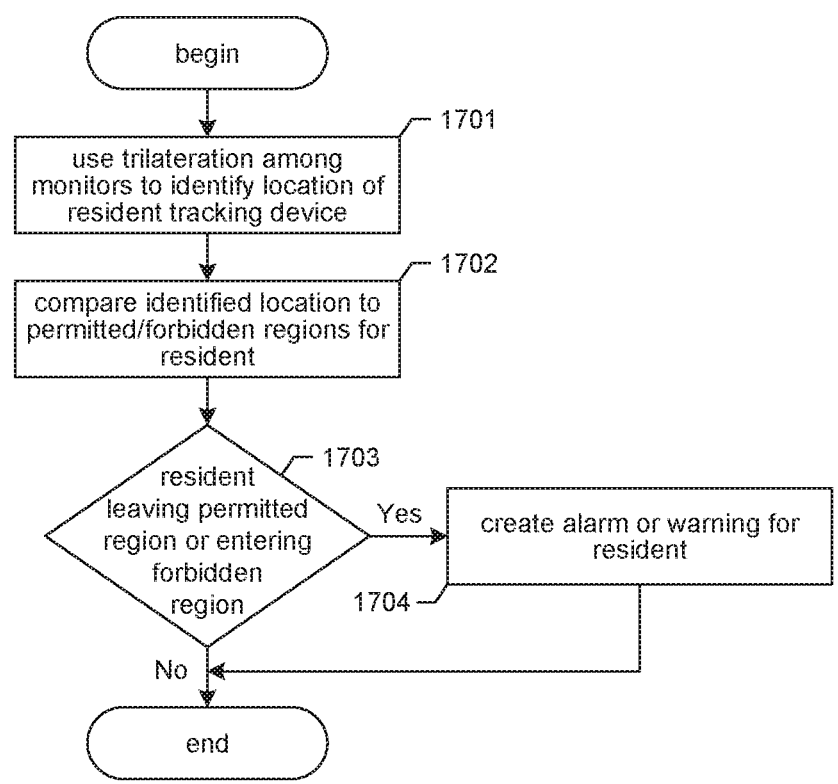
FIG. 17 is a flow diagram showing a process performed at the facility in some embodiments to track and respond to the location of a resident.

FIG. 17 is a flow diagram showing a process perform the facility in some embodiments to track and respond to the location of a resident. In acts 1701, the facility uses trilateralation among monitor devices to identify the location of a tracking device worn by the resident, such as a pendant or bracelet. In act 1702, the facility compares the location identified in act 1701 to a set of permitted and forbidden regions established for the resident. For example, the resident's room and bathroom may be permitted regions, and a building exit stairway may be a forbidden region. In act 1703, if the comparison of act 1702 indicates that the resident is leaving a permitted region or entering a forbidden region, then the facility continues in act 1704, else this process concludes. In act 1704, the facility creates an alarm or warning for the resident reflecting of their leaving of a permitted region or entering a forbidden region. After act 1704, this process concludes.

In some embodiments, the facility tracks the physical location of staff members in the same or similar ways—using mobile devices carried by staff members, RFID badges worn by staff members, etc.—such as to monitor their performance of rounds, alarm and warning responses, and other responsibilities that involve movement through the health care facility. In some embodiments, the facility uses various types of interactions by staff members with monitor devices, such as pressing a button on the monitor device, passing near the monitoring device carrying a wireless-enabled portable device such as one actively observing or broadcasting the Bluetooth Low Energy ("BLE") protocol; receiving location determined by the portable device using Global Positioning System ("GPS") or Indoor Positioning System ("IPS"), affirmative room check-in using an app running on the portable device, or some combination of some or all of these.

In some embodiments, the location-tracking of staff members is used by the facility as a basis for assigning alerts to staff members, such as by assigning an alert for a particular location first to the nearest staff member, then to the second-nearest staff member, etc.

In some embodiments, the alarm may be prevented entirely by combining monitor status with staff location. For example, if a staff member is located in the room and by the bed at the time of a bed alarm, in some embodiments the facility infers that the staff member is actively working with the resident in the room. In some embodiments, in making this inference, the facility relies on on-body detection by the device being carried by the staff member to reduce the possibility that a device accidentally left behind will cause valid alarms to inadvertently be suppressed.

Health Care Facilities

In various embodiments, the facility operates in health care facilities of a variety of types, including, for example, nursing homes, care homes, hospitals, hospice centers, birthing centers, prison health care centers, independent living centers, rehabilitation centers, etc.

Home Use

In some embodiments, a version of the facility is adapted for home use, such as on behalf of an aged or unhealthy person who lives alone, or is otherwise at home alone during extended periods. In some embodiments, when the facility identifies an alarm, it dispatches it to people outside the home, such as the person's children, neighbors, friends, or clergy. These alarms may be via text message, email message, telephone call using a recorded or synthesized voice, facsimile message, smartphone app, etc. In some embodiments, some or all of these ad hoc caregivers can access reports and event histories generated by the facility for the monitored person, such as via the public web, in some cases subject to authentication and/or secure transmission protocols.

CONCLUSION

It will be appreciated by those skilled in the art that the above-described facility may be straightforwardly adapted or extended in various ways. While the foregoing description makes reference to particular embodiments, the scope of the invention is defined solely by the claims that follow and the elements recited therein.

We claim:

1. One or more computer memories collectively having contents configured to cause a mobile device configured to be carried by a caregiver at a residential facility to perform a method, the method comprising:
displaying, via a user interface of the mobile device, information identifying a location in which a resident of the residential facility is predicted to be in need of assistance at a future time, wherein the prediction is based on output from sensors near the identified location, and wherein the mobile device is remote from the resident and is selected from a plurality of mobile devices based on (a) a proximity between the identified location and a location of the mobile device and (b) a period of time during which the caregiver has not responded to the predicted need of assistance;
displaying, via the user interface, a control activatable to indicate that a person carrying the mobile device is undertaking to provide assistance in the identified location;
displaying another control activatable to indicate that the person carrying the mobile device will not undertake to provide assistance in the identified location;
receiving input activating the displayed other control to indicate that the person carrying the mobile device will not undertake to provide assistance in the identified location; and
in response to receiving the input, contemporaneously with receiving the input, sending to a server a notification identifying the mobile device that reflects receiving the input.

2. The computer memories of claim 1, the method further comprising:
receiving input activating the displayed control; and
in response to receiving the input, contemporaneously with receiving the input, sending to a server a notification identifying the mobile device that reflects receiving the input.

3. The computer memories of claim 1, the method further comprising:
receiving first input activating the control; and
in response to receiving the first input, displaying a second control activatable to indicate that the person carrying the mobile device has completed a visit to the identified location.

4. The computer memories of claim 3, the method further comprising:
receiving input activating the second control; and
in response to receiving the input activating the second control, displaying a survey seeking information about the visit to the identified location.

5. The computer memories of claim 4, the method further comprising:
receiving input responding to the survey; and
sending to a server a representation of the input responded to the survey.

6. The computer memories of claim 1, wherein the resident of the residential facility is predicted to be in need of assistance based, at least in part, on one inference rule selected from a plurality of inference rules.

7. A method, comprising:
displaying, via a mobile device, information identifying a location in which a resident of a residential facility is predicted to be in need of assistance at a future time, wherein the prediction is based on output from sensors near the identified location, and wherein the mobile device is remote from the resident and is selected from a plurality of mobile devices based on (a) a proximity between the identified location and a location of the mobile device and (b) a period of time during which a caregiver associated with the mobile device has not responded to the predicted need of assistance;
displaying, via the mobile device, a control activatable to indicate that a person carrying the mobile device is undertaking to provide assistance in the identified location;
displaying another control activatable to indicate that the person carrying the mobile device will not undertake to provide assistance in the identified location;
receiving input activating the displayed other control to indicate that the person carrying the mobile device will not undertake to provide assistance in the identified location; and
in response to receiving the input, contemporaneously with receiving the input, sending to a server a notification identifying the mobile device that reflects receiving the input.

8. The method of claim 7, further comprising:
receiving input activating the displayed control; and
in response to receiving the input, contemporaneously with receiving the input, sending to a server a notification identifying the mobile device that reflects receiving the input.

9. The method of claim 7, further comprising:
receiving first input activating the control; and
in response to receiving the first input, displaying a second control activatable to indicate that the person carrying the mobile device has completed a visit to the identified location.

10. The method of claim 9, further comprising:
receiving input activating the second control; and
in response to receiving the input activating the second control, displaying a survey seeking information about the visit to the identified location.

11. The method of claim 10, further comprising:
receiving input responding to the survey; and
sending to a server a representation of the input responded to the survey.

12. The method of claim 7, wherein the resident of the residential facility is predicted to be in need of assistance based, at least in part, on one inference rule selected from a plurality of inference rules.

13. A system, comprising:
one or more processors; and
memory storing contents that, when executed by the one or more processors, cause the system to perform actions comprising:
displaying, via a mobile device, information identifying a location in which a resident of the residential facility is predicted to be in need of assistance at a future time, wherein the prediction is based on output from sensors near the identified location, and wherein the mobile device is remote from the resident and is selected from a plurality of mobile devices based on (a) a proximity between the identified location and a location of the mobile device and (b) a period of time during which a caregiver associated with the mobile device has not responded to the predicted need of assistance;

displaying, via the mobile device, a control activatable to indicate that a person carrying the mobile device is undertaking to provide assistance in the identified location;

displaying another control activatable to indicate that the person carrying the mobile device will not undertake to provide assistance in the identified location;

receiving input activating the displayed other control to indicate that the person carrying the mobile device will not undertake to provide assistance in the identified location; and in response to receiving the input, contemporaneously with receiving the input, sending to a server a notification identifying the mobile device that reflects receiving the input.

14. The system of claim 13, the actions further comprising:

receiving input activating the displayed control; and in response to receiving the input, contemporaneously with receiving the input, sending to a server a notification identifying the mobile device that reflects receiving the input.

\* \* \* \* \*